United States Patent
Goodall et al.

(10) Patent No.: US 8,321,236 B2
(45) Date of Patent: Nov. 27, 2012

(54) METHOD AND APPARATUS FOR PRESCRIPTION PROCESSING

(75) Inventors: Charles Goodall, Hawthorn Woods, IL (US); Sam Libo, Deerfield, IL (US); Peter Liccardo, Palatine, IL (US); Dejan Kozic, Wadsworth, IL (US)

(73) Assignee: Walgreen Co., Deerfield, IL (US)

( * ) Notice: Subject to any disclaimer, the term of this patent is extended or adjusted under 35 U.S.C. 154(b) by 2238 days.

(21) Appl. No.: 10/353,277

(22) Filed: Jan. 29, 2003

(65) Prior Publication Data

US 2003/0149599 A1 Aug. 7, 2003

Related U.S. Application Data

(60) Provisional application No. 60/353,983, filed on Feb. 1, 2002.

(51) Int. Cl.
*G06Q 50/00* (2012.01)
(52) U.S. Cl. .................................. 705/2; 705/3
(58) Field of Classification Search .................. 705/2, 3, 705/4; 283/81; 700/216, 222, 2, 225, 231, 700/235, 237, 244; 379/88.16; 235/375; 221/9, 92
See application file for complete search history.

(56) References Cited

U.S. PATENT DOCUMENTS

| | | | |
|---|---|---|---|
| 4,852,001 A | 7/1989 | Tsushima et al. | |
| 4,918,604 A * | 4/1990 | Baum | 221/5 |
| 4,958,280 A * | 9/1990 | Pauly et al. | 705/3 |
| 5,053,970 A | 10/1991 | Kurihara et al. | |
| 5,072,383 A | 12/1991 | Brimm et al. | |
| 5,208,762 A * | 5/1993 | Charhut et al. | 700/216 |
| 5,260,868 A | 11/1993 | Gupta et al. | |
| 5,289,370 A | 2/1994 | Lirov | |
| 5,337,919 A | 8/1994 | Spaulding et al. | |
| 5,548,518 A | 8/1996 | Dietrich et al. | |
| 5,559,710 A | 9/1996 | Shahraray et al. | |
| 5,597,995 A * | 1/1997 | Williams et al. | 235/375 |
| 5,615,121 A | 3/1997 | Babayev et al. | |
| 5,619,991 A | 4/1997 | Sloane | |

(Continued)

FOREIGN PATENT DOCUMENTS

EP 0921 488 A1 6/1999

(Continued)

OTHER PUBLICATIONS

Bar Codes Effect Liquor Distribution Efficiency, May 1995, Packaging Digest, v. 32, n6, p26(3).*

(Continued)

*Primary Examiner* — Gerald J. O'Connor
*Assistant Examiner* — Natalie A Pass
(74) *Attorney, Agent, or Firm* — Francis C. Kowalik; Marshall, Gerstein & Borun LLP; Randall G. Rueth

(57) ABSTRACT

A method and an apparatus for processing a prescription order are described herein. A prescription label for the prescription order may be generated in response to receipt of the prescription order. The prescription label being generated in a priority order based on a plurality of pharmacy factors. The prescription order may be filled according to the priority order based on the plurality of pharmacy factors. Based on the prescription label, a plurality of graphic displays may be generated to verify the prescription order. The patient may be notified of the status of the prescription associated with the prescription order based on the plurality of graphic displays.

28 Claims, 14 Drawing Sheets

U.S. PATENT DOCUMENTS

| | | |
|---|---|---|
| 5,737,539 A | 4/1998 | Edelson et al. |
| 5,737,728 A | 4/1998 | Sisley et al. |
| 5,748,907 A | 5/1998 | Crane |
| 5,758,095 A | 5/1998 | Albaum et al. |
| 5,765,139 A | 6/1998 | Bondy |
| 5,790,785 A | 8/1998 | Klug et al. |
| 5,797,515 A | 8/1998 | Liff et al. |
| 5,801,755 A | 9/1998 | Echerer |
| 5,826,236 A | 10/1998 | Narimatsu et al. |
| 5,826,252 A | 10/1998 | Wolters, Jr. et al. |
| 5,842,976 A | 12/1998 | Williamson |
| 5,845,255 A | 12/1998 | Mayaud |
| 5,852,259 A | 12/1998 | Yanase et al. |
| 5,907,493 A | 5/1999 | Boyer et al. |
| 5,911,687 A | 6/1999 | Sato et al. |
| 5,915,240 A | 6/1999 | Karpf |
| 5,924,074 A | 7/1999 | Evans |
| 5,946,883 A | 9/1999 | Yuyama et al. |
| 5,950,630 A * | 9/1999 | Portwood et al. ............. 128/897 |
| 5,954,640 A | 9/1999 | Szabo |
| 5,963,453 A * | 10/1999 | East ............... 700/244 |
| 5,963,911 A | 10/1999 | Walker et al. |
| 5,970,462 A | 10/1999 | Reichert |
| 5,974,393 A | 10/1999 | McCullough et al. |
| 5,987,519 A | 11/1999 | Peifer et al. |
| 6,067,524 A | 5/2000 | Byerly et al. |
| 6,104,798 A | 8/2000 | Lickiss et al. |
| 6,112,182 A | 8/2000 | Akers et al. |
| 6,181,979 B1 * | 1/2001 | Murakami ............... 700/216 |
| 6,202,923 B1 | 3/2001 | Boyer et al. |
| 6,208,973 B1 | 3/2001 | Boyer et al. |
| 6,292,786 B1 | 9/2001 | Deaton et al. |
| 6,294,999 B1 | 9/2001 | Yarin et al. |
| 6,311,163 B1 | 10/2001 | Sheehan et al. |
| 6,330,491 B1 | 12/2001 | Lion |
| 6,347,329 B1 | 2/2002 | Evans |
| 6,364,517 B1 | 4/2002 | Yuyama et al. |
| 6,370,841 B1 | 4/2002 | Chudy et al. |
| 6,381,577 B1 | 4/2002 | Brown |
| 6,397,190 B1 | 5/2002 | Goetz |
| 6,421,650 B1 | 7/2002 | Goetz et al. |
| 6,438,451 B1 | 8/2002 | Lion |
| 6,463,417 B1 | 10/2002 | Schoenberg |
| 6,464,142 B1 | 10/2002 | Denenberg et al. |
| 6,477,442 B1 | 11/2002 | Valerino, Sr. |
| 6,493,427 B1 | 12/2002 | Kobylevsky et al. |
| 6,496,427 B2 | 12/2002 | Kojima et al. |
| 6,523,009 B1 | 2/2003 | Wilkins |
| 6,530,518 B1 * | 3/2003 | Krichilsky et al. ......... 235/375 |
| 6,539,281 B2 | 3/2003 | Wan et al. |
| 6,539,360 B1 | 3/2003 | Kadaba |
| 6,564,121 B1 | 5/2003 | Wallace et al. |
| 6,591,243 B1 * | 7/2003 | Grettve et al. ............... 705/8 |
| 6,625,952 B1 | 9/2003 | Chudy et al. |
| 6,711,460 B1 | 3/2004 | Reese |
| 6,735,497 B2 | 5/2004 | Wallace et al. |
| 6,874,684 B1 | 4/2005 | Denenberg et al. |
| 6,917,922 B1 | 7/2005 | Bezos et al. |
| 7,111,780 B2 | 9/2006 | Broussard et al. |
| 7,139,639 B2 | 11/2006 | Broussard et al. |
| 7,337,129 B1 | 2/2008 | Lowry et al. |
| 2001/0009005 A1 | 7/2001 | Godin et al. |
| 2001/0028304 A1 | 10/2001 | I'Anson et al. |
| 2001/0047285 A1* | 11/2001 | Borders et al. ............... 705/8 |
| 2002/0052762 A1* | 5/2002 | Kobylevsky et al. ......... 705/2 |
| 2002/0062175 A1 | 5/2002 | Lion |
| 2002/0062230 A1 | 5/2002 | Morag et al. |
| 2002/0103726 A1* | 8/2002 | Jones et al. ............... 705/28 |
| 2002/0120573 A1 | 8/2002 | McCormick |
| 2002/0130065 A1 | 9/2002 | Bloom |
| 2002/0147642 A1 | 10/2002 | Avallone et al. |
| 2002/0153411 A1 | 10/2002 | Wan et al. |
| 2002/0161658 A1 | 10/2002 | Sussman |
| 2002/0174025 A1 | 11/2002 | Hind et al. |
| 2002/0188467 A1 | 12/2002 | Eke |
| 2003/0018495 A1* | 1/2003 | Sussman ............... 705/2 |
| 2003/0074234 A1 | 4/2003 | Stasny |
| 2003/0132298 A1 | 7/2003 | Swartz et al. |
| 2003/0149599 A1 | 8/2003 | Goodall et al. |
| 2003/0179287 A1 | 9/2003 | Kozic et al. |
| 2003/0188200 A1 | 10/2003 | Paquin et al. |
| 2004/0019502 A1 | 1/2004 | Leaman et al. |
| 2004/0078231 A1 | 4/2004 | Wilkes et al. |
| 2004/0133705 A1 | 7/2004 | Broussard et al. |
| 2004/0172289 A1 | 9/2004 | Kozic et al. |
| 2004/0220829 A1 | 11/2004 | Baharav et al. |
| 2004/0221034 A1 | 11/2004 | Kausik et al. |
| 2004/0260577 A1 | 12/2004 | Dahlin et al. |
| 2005/0102203 A1* | 5/2005 | Keong ............... 705/28 |
| 2006/0041330 A1 | 2/2006 | Ansari et al. |
| 2006/0276933 A1 | 12/2006 | Chavez et al. |

FOREIGN PATENT DOCUMENTS

| | | |
|---|---|---|
| EP | 1096364 A2 * | 5/2001 |
| JP | 11095940 A * | 4/1999 |
| WO | WO-96 13790 | 5/1996 |
| WO | WO-0108393 A1 | 2/2001 |
| WO | WO 3037637 A1 * | 5/2003 |

OTHER PUBLICATIONS

Anonymous, "CVS, Merck-Medco in E-commerce Alliance," Chain Drug Review, 21(18):2 (1999).

Anonymous, "Name Change Reflects CVS' Commitment to E-commerce," Chain Drug Review, 21(15):2 (1999).

Walgreens On-line Prefills (Website Printout Packet-printed Jul. 5, 2006) archived as Jun. 17, 1998, p. 1-13.

Office action for U.S. Appl. No. 11/697,783 dated Sep. 29, 2010.

Colchamiro, "Independents Look to Go Online," American Druggist, Sep. 1999, pp. 1-3.

McNaughton, "Can Net Drugstores Outpace the Chains?" CNET News.com, Feb. 24, 1999, 1 page.

Wolverton, "Online Pharmacies Partner for Power," CNET News.com, Oct. 8, 1999, pp. 1-2.

"The Virtual Pharmacist," Rural Electric, vol. 60, No. 6, Mar. 2002, p. 20.

U.S. Appl. No. 09/715,872, filed Nov. 15, 2000, entitled "Apparatus and Method for Accessing Pharmacy Information and Ordering Prescriptions."

U.S. Appl. No. 11/253,252, filed Oct. 18, 2005, entitled "System for Separating and Distributing Pharmacy Order Processing."

U.S. Appl. No. 11/252,759, filed Oct. 18, 2005, entitled "System for Separating and Distributing Pharmacy Order Processing for Medication Payments."

U.S. Appl. No. 11/252,776, filed Oct. 18, 2005, entitled "System for Separating and Distributing Pharmacy Order Processing for Specialty Medication."

U.S. Appl. No. 11/253,185, filed Oct. 18, 2005, entitled "System for Separating and Distributing Pharmacy Order Processing for Prescription Verification."

U.S. Appl. No. 11/253,253, filed Oct. 18, 2005, entitled "System for Separating and Distributing Pharmacy Order Processing for Out of Stock Medication."

U.S. Appl. No. 11/252,947, filed Oct. 18, 2005, entitled "System for Separating and Distributing Pharmacy Order Processing for Compound Medication."

U.S. Appl. No. 11/252,775, filed Oct. 18, 2005, entitled "Method and Apparatus for Inter-Pharmacy Workload Balancing."

* cited by examiner

TeamRx - [Priority Exceptions]

Highest Priority Exception
- Type: CMD
- Promised Time: FRI 04/06/01 11:40 AM
- Exc Created at: FRI 04/06/01 11:20 AM
- Rx Nbr: 12762
- Drug Name: KAOPECTATE P-MINT 240ML

Contact Info
- Patient: ALEXIS D TOCQUEVILLE
- Birthdate: 01/01/1955
- Address: 1835 RUE AMERIQUE
- Patient Phone: (312) 690-5486
- Prescriber: DR. DROM
- Prescriber Phone: (312) 123-3221
- Plan Name: <NONE>
- Plan Phone:

Resolution
To resolve this exception, use the "Call Pbr" pushbutton below to request additional refills from the prescriber
Did the prescriber approve additional refills?

[Approved] [Denied] [Will Call Back]

[Close]

FIG. 8

METHOD AND APPARATUS FOR PRESCRIPTION PROCESSING

CROSS REFERENCE TO RELATED APPLICATION

This application is a non-provisional application claiming priority from Provisional Application Ser. No. 60/353,983, entitled "Method and Apparatus for Prescription Processing" filed Feb. 1, 2002.

TECHNICAL FIELD

The present disclosure relates generally to pharmaceutical services, and more particularly to, a method and apparatus for processing a prescription from receipt of the prescription order to delivery of the prescription to the patient.

BACKGROUND

Pharmacies have traditionally used labor intensive methods of accepting, prioritizing, and dispensing prescriptions requested by patients, physicians, nurses, physician assistants, and others. For example, a typical prescription scenario may include a patient visiting a pharmacy to request that a prescription be filled. If the patient does not wait for the prescription to be filled then a subsequent phone call by a pharmacy staff member may notify the patient when the prescription has been filled and is ready for pick-up. A return visit by the patient to pickup the prescription may follow.

Each step of the typical prescription scenario requires interaction between the patient and the pharmacy staff. In addition, many steps are required to be performed by the pharmacy staff between the time that the prescription is ordered and the time the prescription is delivered to the patient. Upon receipt of the request, a variety of tasks may be performed such as, but not limited to, logging the prescription order into the prescription system, checking the availability of the drug for the prescription order, prioritizing in time the prescription order with other prescription orders, verifying insurance coverage, checking for the possibility of using a generic drug substitute, placing one or more phone calls to the prescriber, checking for the possibility of drug interactions, checking for a patient's drug sensitivity, dispensing the proper drug in the proper quantity, and printing and affixing labels to the prescription. Thus, the efficiency of the prescription workflow is important to the success and profitability of a pharmacy.

The safety of patients is also important to the success and profitability of the pharmacy. Ensuring patient safety requires that the pharmacy staff have expertise in a variety of areas. In addition to medical expertise, for example, a pharmacist must possess the organizational skills necessary to manage a high volume of prescriptions while ensuring that each patient's prescription is properly dispensed at the proper dosage level and in the proper amount. This requires a timely flow of both patient and prescription information in an easy-to-understand format to the pharmacy staff during the time between receiving the prescription order and delivering the prescription to the patient ("order-to-delivery"). Further, this also requires the timely flow of both patient and prescription information in an easy-to-understand format to the patient and the prescriber.

In addition to efficiency and patient safety, patient satisfaction and patient loyalty are important factors in determining the success of the pharmacy. Quick delivery of the prescription to the patient is one way of ensuring patient satisfaction. If quick delivery of the prescription is not possible then adherence to promised delivery time may suffice. In that case, the patient will know when he or she may pick-up the prescription. Accordingly, the patient will not have to make repeated trips to the pharmacy.

A few systems have been developed to assist pharmacy staffs in the tasks associated with accepting, prioritizing, and dispensing prescriptions. However, these systems have primarily been directed to discrete tasks such as allowing patient and prescriber access to prescription ordering using the Internet or e-mail. Further, current systems do not address the overall flow of the process from receipt of the prescription order to delivery of the prescription to the patient.

BRIEF DESCRIPTION OF THE DRAWINGS

FIGS. 7 and 8 are graphic displays to show the types and the numbers of priority exceptions;

DETAILED DESCRIPTION

In general, the system described herein allows the pharmacy staff to efficiently manage a high volume prescription workload from receipt of the prescription order to delivery of the prescription to the patient and to maintain high patient safety standards. In operation, (1) a prescription order is received and entered into a prescription workflow or work queue, (2) based on numerous pharmacy factors, a promised time is calculated and assigned to the prescription or an override promised time is assigned based on information from the patient, and (3) the prescription is filled and verified. Any outstanding tasks or problems associated with the prescription (hereinafter referred to as "exceptions") are timely displayed to the pharmacy staff in an easy-to-understand format to mitigate delays that may be associated with the exceptions.

Figure 1:
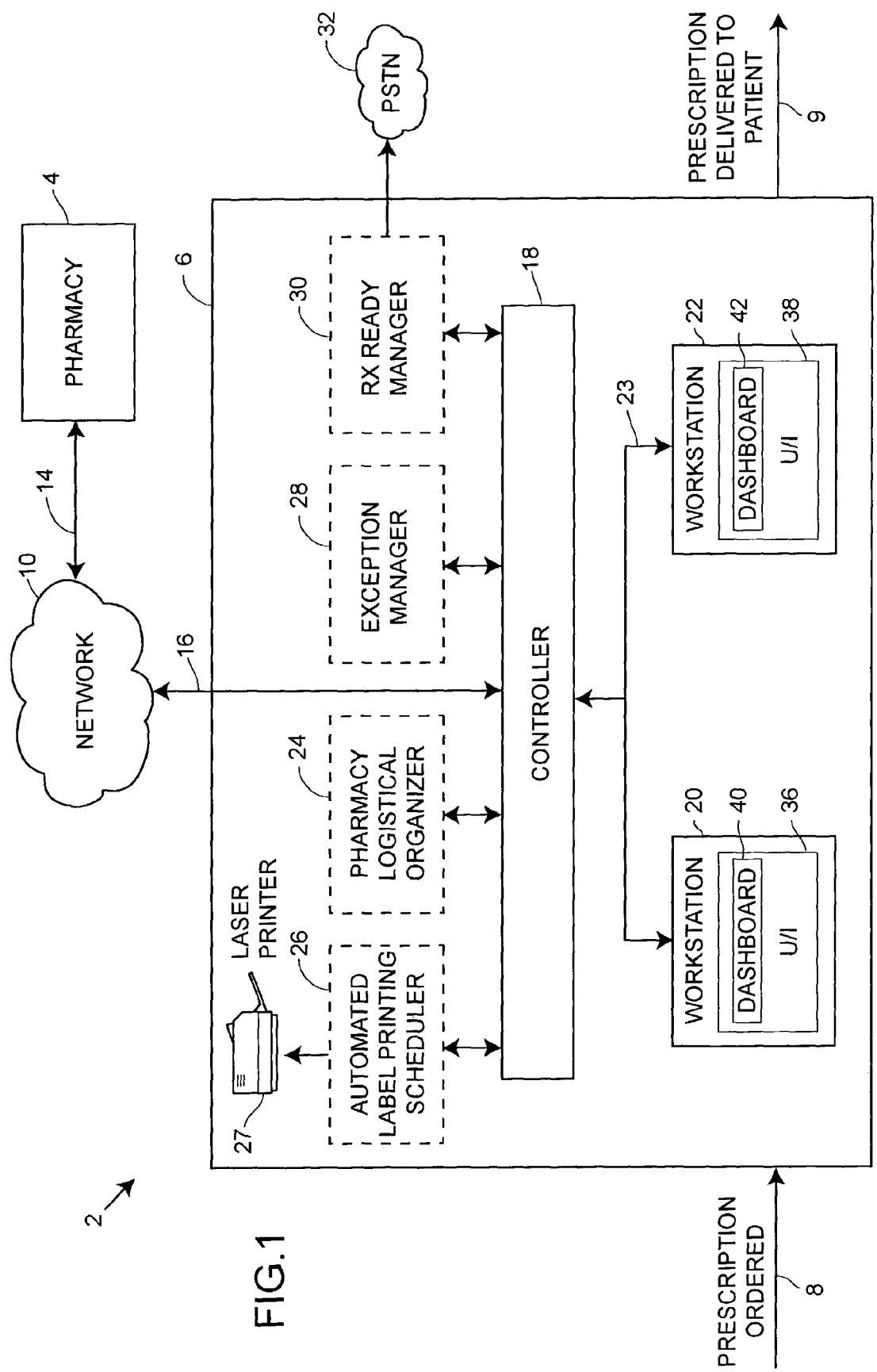
FIG. 1 is a high level block diagram of a pharmacy network system.

FIG. 1 illustrates an embodiment of a pharmacy network system 2 constructed to manage a high volume prescription workload. Referring to FIG. 1, the pharmacy network system 2 may include multiple pharmacies or facilities, generally shown as 4 and 6, operatively coupled to a network 10 via multiple network data links 14, 16. The pharmacies 4, 6 may be located in different areas of the same city, in different cities, or in different states. The network 10 may be provided using a wide variety of techniques known to persons of ordinary skill in the art to transfer pharmacy data that includes, but is not limited to, prescription information, patient information, and provider information. For example, the network 10 may include, but is not limited to, dedicated access lines, plain ordinary telephone (POT) lines, satellite links, and combinations of such lines and/or links. The network 10 may also include a plurality of network computers or server computers (not shown), each of which may be operatively interconnected. Where the network 10 comprises the Internet, data communication may take place via the network data links 14, 16 in accordance with an Internet communication protocol.

Figure 2:
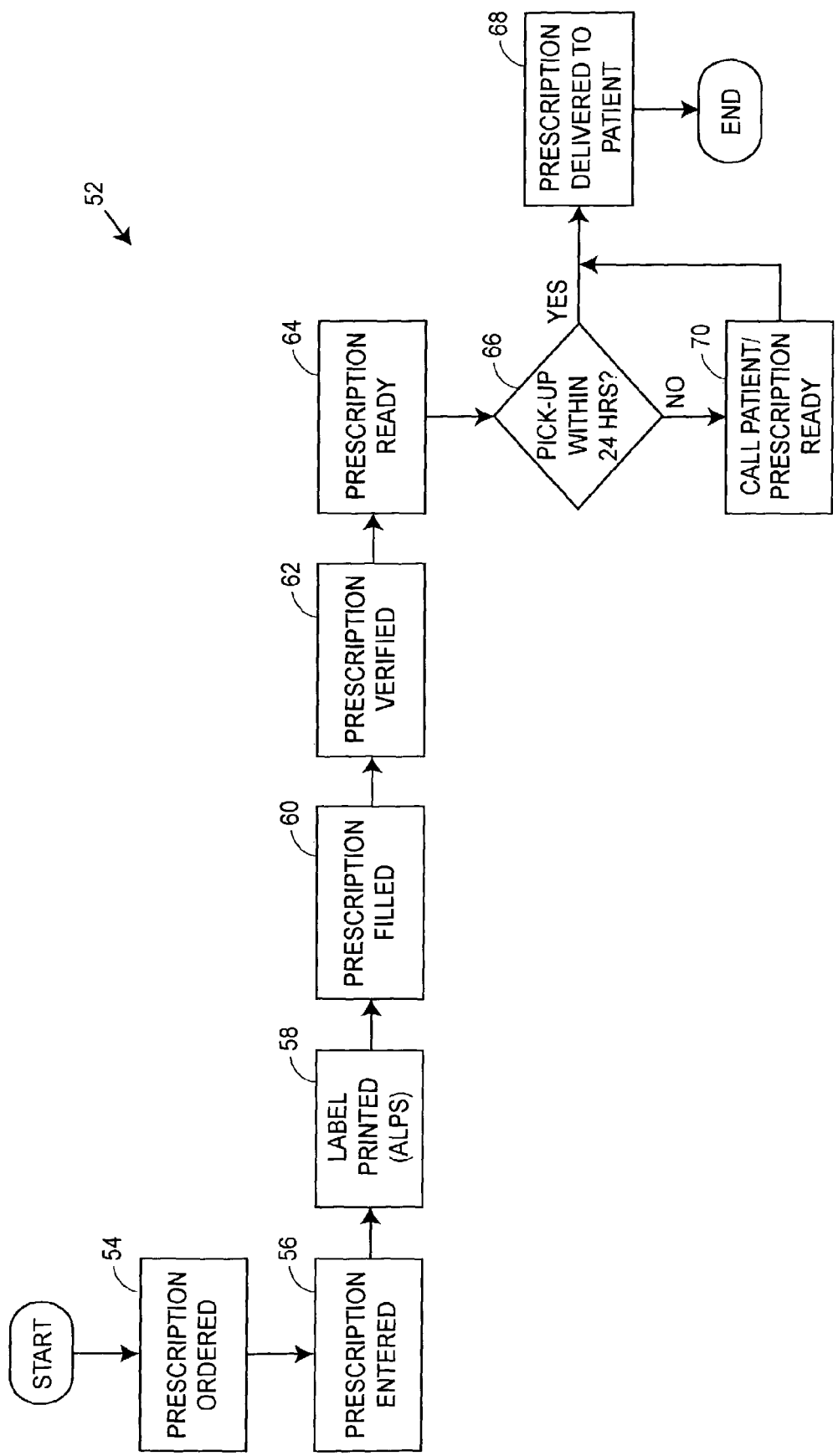
FIG. 2 is a high level flowchart of a prescription workflow from receipt of the prescription order to delivery of the prescription to the patient.

The pharmacies 4, 6 are configured to facilitate a method for managing an efficient prescription workflow from receipt of a prescription order 8 to delivery of the prescription to a patient 9. FIG. 2 illustrates the steps of the prescription workflow 52 from receipt of the prescription order 8 at a block 54 to delivery of the prescription to the patient 9 at a block 68. Upon receipt of the prescription order at the block 54, the prescription order enters the prescription workflow 52 at a block 56 in one of a number of ways, depending on how the prescription order was received. For example, the prescription order may enter the prescription workflow 52 via manual entry by a pharmacy staff member, via an electronic data interchange (EDI) transmission from a physician's office, via an Internet entry by a patient (e.g., www.walgreens.com), or via a touch-tone telephone prescription entry by the patient. In addition, the prescription order may enter into the prescription workflow 52 via automatic entry, i.e., set up in a pharmacy system computer to automatically initiate a refill of a prescription when a predetermined number of days has elapsed since the last delivery to the patient.

After the prescription order has been entered into the prescription workflow 52 at the block 56, the prescription order and other associated prescription information (i.e., prescription drug information, patient information, prescriber information, and special instructions) are routed to an automated label printing scheduler (ALPS, which is shown as 26 in FIG. 1) at a block 58 (discussed below in connection with FIGS. 4, 5, and 6). At the block 58, the ALPS 26 may produce a printed prescription label having a front side and a back side that includes, but is not limited to, a bar code associated with the prescription order. The time at which the prescription label is automatically printed is based on a number of factors such as, but not limited to, the promised time for delivery of the prescription to the patient, the current volume of additional prescription orders to be prepared in a 24-hour time period, an identification parameter associated with the patient such as the patient's primary phone number or last name, and the pharmacy workload (i.e., whether is pharmacy is experiencing peak prescription traffic hours).

Based on the chronological order that the prescription labels were printed, a pharmacist or a pharmacy technician fills the prescription orders corresponding to the printed prescription labels at a block 60. Thus, the ALPS 26 determines the order in which the prescription order is filled relative to other prescription orders in addition to printing the prescription labels. After the labeled prescription is filled at the block 60, the prescription is verified by a pharmacist at a block 62. The verification step includes, inter alia, a bar code scan that produces a visual display of patient/prescription information on a graphic user interface (GUI) that is reviewed and compared to the filled prescription by the pharmacist to ensure patient safety. Upon completion of the verification step, the prescription is ready for patient pick-up at a block 64 if there are no unresolved tasks or problems associated with filling and verifying the prescription order (hereinafter referred to as "exceptions" discussed in connection with FIGS. 7 and 8). If the prescription is picked-up by the patient, the patient's family member, or friend within 24 hours of being ready or after its promised time, the prescription has been "delivered" to the patient at a block 68. However, if the prescription is not picked-up by the patient, the patient's family member, or friend within 24 hours of being ready or after its promised time, the patient is notified that the prescription is ready for pick-up at a block 70.

The occurrence of an exception(s) may have a delaying effect on the overall prescription workflow. The length of the delay is typically related to pharmacy staff handling of the exception. For example, if a third party insurance company indicates that it will deny payment for the prescription, a pharmacy staff member often may notify the patient to arrange alternate payment methods. In some cases, the time delay introduced by the required notification to the patient increases the overall time period between receipt of the prescription order and delivery of the prescription to the patient, which adversely affects delivery of the prescription before or at the prescription's promised time.

However, timely notification to the patient is often contingent on the availability of the relevant information to a pharmacy staff member, which requires that the relevant information be presented to the pharmacy staff member quickly and in an easy-to-understand format. Thus, efficiently and affectively presenting "exception" information to the pharmacy staff member enables quick notification to the patient to prevent payment delays associated with third-party payment denials.

In some cases, possible drug interaction between the patient's prescription and the patient's current medication may be uncovered. Immediate notification of the possible drug interaction is necessary—both to the pharmacy staff member and the patient. Obviously, presenting the drug interaction information to the pharmacy staff member in an easy-to-understand format may mitigate possible delays associated with notifying the patient and/or the patient's prescription.

Referring again to FIG. 1, the pharmacy 6 of the pharmacy network system 2 includes a controller 18 operatively connected to workstations, generally shown as 20 and 22, via a network link 23. The network link 23 may be a wide area network (WAN), a local area network (LAN), or any other type of network known to persons of ordinary skill in the art. The workstation 20 includes a user interface (U/I) 36 configured to assist pharmacy staff members in performing their duties and to display graphics. Similarly, the workstation 22 includes a user interface 38. Further, a central pharmacy database (not shown) configured to store patient information (e.g., customer preferences, and other drugs the patient may be taking) is operatively coupled to the controller 18.

The pharmacy 6 also includes a pharmacy logistical organizer 24, an ALPS 26 operatively coupled to a printer 27, an exception manager 28, and a prescription-ready manager (Rx-ready manager) 30 operatively coupled to a public switched telephone network (PSTN) 32. The printer 27 may be any type of printer capable of generating prescription labels and associated prescription information (e.g., a laser printer).

Although the pharmacy logistical organizer 24, the ALPS 26, the exception manager 28, and the Rx-ready manager 30 are shown as being operatively connected to the controller 18, those components of the pharmacy 6 may reside as software within the controller 18 (i.e., stored on a tangible medium such as a CD-ROM, a floppy disk, a hard drive, a digital versatile disk (DVD), or a memory). In addition, persons of ordinary skill in the art will readily appreciate that one or more of the pharmacy logistical organizer 24, the ALPS 26, the exception manager 28, and the Rx-ready manager 30 could alternatively be implemented by hardware and/or firmware in a well known manner.

In particular, the pharmacy logistical organizer 24 is representative of a method for coordinating the steps (see FIG. 2) of managing the prescription workflow from receipt of each prescription order to delivery of the prescription to the patient while maintaining high patient safety standards. The ALPS 26 is representative of a method for automatically prioritizing prescription orders based on a number of factors, and directing the printer 27 to print the correct number of prescription labels at the correct time in batches based on the priority of the prescription orders. Accordingly, operation of the ALPS 26 contributes to ensuring a steady prescription workflow throughout the day. The exception manager 28 is representative of a method for automatically identifying and ranking prescription orders which have one or more exceptions (hereinafter referred to as a "prescription/exception") that must be resolved prior to prescription delivery to the patient. For example, a prescription/exception may include a prescription refill that requires a doctor's approval before filling. The exception manager 28 will automatically assign a higher priority to a prescription/exception scheduled for patient pickup within the hour than it will assign to a same prescription/exception scheduled for patient pick-up the following day. Thus, the exception manager 28 assists the pharmacy staff with task prioritization in a high volume prescription workflow environment of the pharmacy 6.

The Rx-ready manager 30 is representative of a method for automatic patient notification when the patient's prescription will not be ready for pick-up at its promised time (i.e., a not-ready notification). Prescriptions that are candidates for the Rx-ready manager 30 include (1) those prescriptions/exceptions that were not resolved prior to their promise time, (2) those prescriptions which have printed labels and have been filled but are not yet verified by their promised time, and (3) those prescriptions entered into the system but do not have a printed label by their promised time. The Rx-ready manager 30 is also configured to automatically notify patients who have been previously notified of a not-ready status of their prescription but now their prescription is ready for pick-up (i.e., a now-ready notification). Both the not-ready and now-ready notification occur in any number of ways such as, but not limited to, an automated telephone call to deliver a pre-recorded voice message to the patient, a page to the patient, a short message page to the patient, and e-mail.

Referring again to FIG. 1, a summary status bar (hereinafter referred to as a "dashboard") is displayed on the user interfaces 36, 38 or workstations 20, 22. A dashboard 40 displayed on the user interface 36 and/or a dashboard 42 displayed on the user interface 38 may provide a visual status of prescription orders currently in the prescription workflow 52. The dashboards 40, 42 (shown in detail in FIG. 14) may be configured in any manner suitable to provide an easy-to-understand visual display of the prescription workflow 52. For example, the dashboards 40, 42, may display a status of all prescription/exceptions having promised times of less than an hour or less than four hours. The selected time intervals may be determined by either the exception manager 26 or a pharmacy staff member. The dashboards 40, 42 may provide an easy-to-understand indication of the duration that prescribers are on telephone hold, and awaiting a response from a pharmacy staff member. Further, the dashboards 40, 42 may provide an indication of the duration that patients are on telephone hold awaiting a response from a pharmacy staff member.

Although the pharmacy data network 2 is shown to include one network 10 and two pharmacies 4, 6, it should be understood that different numbers of networks including different numbers of network computers (not shown) and different numbers of pharmacies may be utilized. For example, the network 10 may include multiple network computers operatively coupled to hundreds or thousands of stores.

Figure 3:
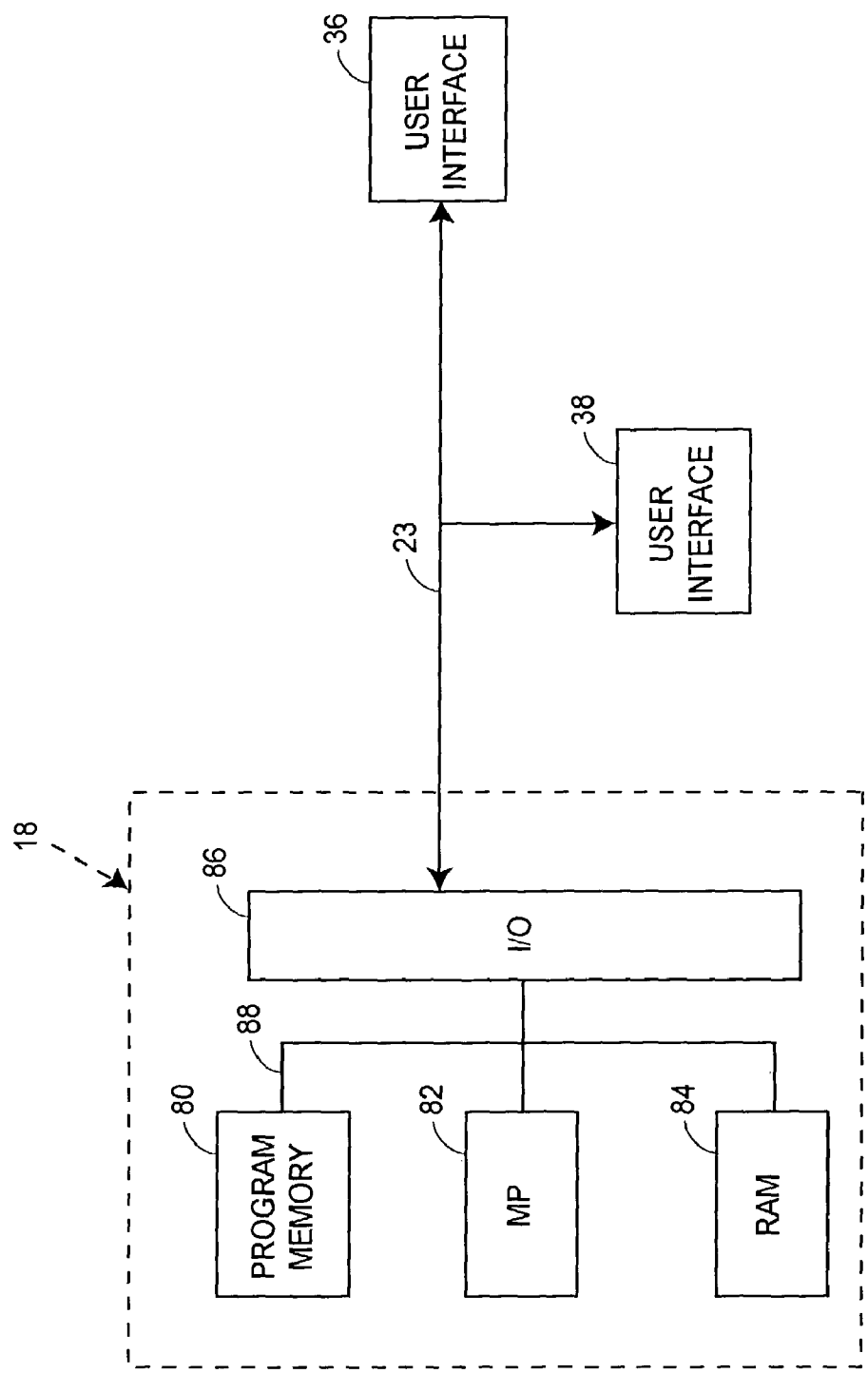
FIG. 3 is a block diagram of the electronic components of the controller shown schematically in FIG. 1.

FIG. 3 is a block diagram of the electronic components of the controller 18 shown schematically in FIG. 1. The controller 18 may include a program memory 80, a micro-controller or a microprocessor (MP) 82, a random access memory (RAM) 84, and an input/output (I/O) circuit 86, all of which may be interconnected via an address/data bus 88. It should be appreciated that although only one microprocessor 82 is shown, the controller 18 may include multiple microprocessors. Similarly, the memory of the controller 18 may include multiple RAMs (one shown as 84) and multiple programs memories (one shown as 80). The RAM(s) and programs memories may be implemented as semiconductor memories, magnetically readable memories, and/or optically readable memories. Although the I/O circuit 86 is shown as a single block, it should be appreciated that the I/O circuit 86 may include a number of different types of I/O circuits. In addition, the controller 18 may be operatively connected to the network 10 via the network data link 16, which may or may not be part of a WAN or a LAN. Further, the controller 18 is operatively coupled to the user interfaces 36, 38.

One manner in which one or more of the pharmacies may optimize a prescription workflow 52 from receipt of the prescription order to delivery of the prescription to the patient is described below in connection with a number of flow charts, which represent a number of portions or routines of one or more computer programs that may be stored in one or more of the memories in the controller 18. The computer program portions or routines may be written at any high level language such as, but not limited to, C, C++, C#, and Java, or any low-level, assembly or machine language. By storing the computer program portions or routines therein, various portions of the memories are physically and/or structurally configured in accordance with the computer program instructions.

Operation of the Automated Label Printing Manager

Figure 4:
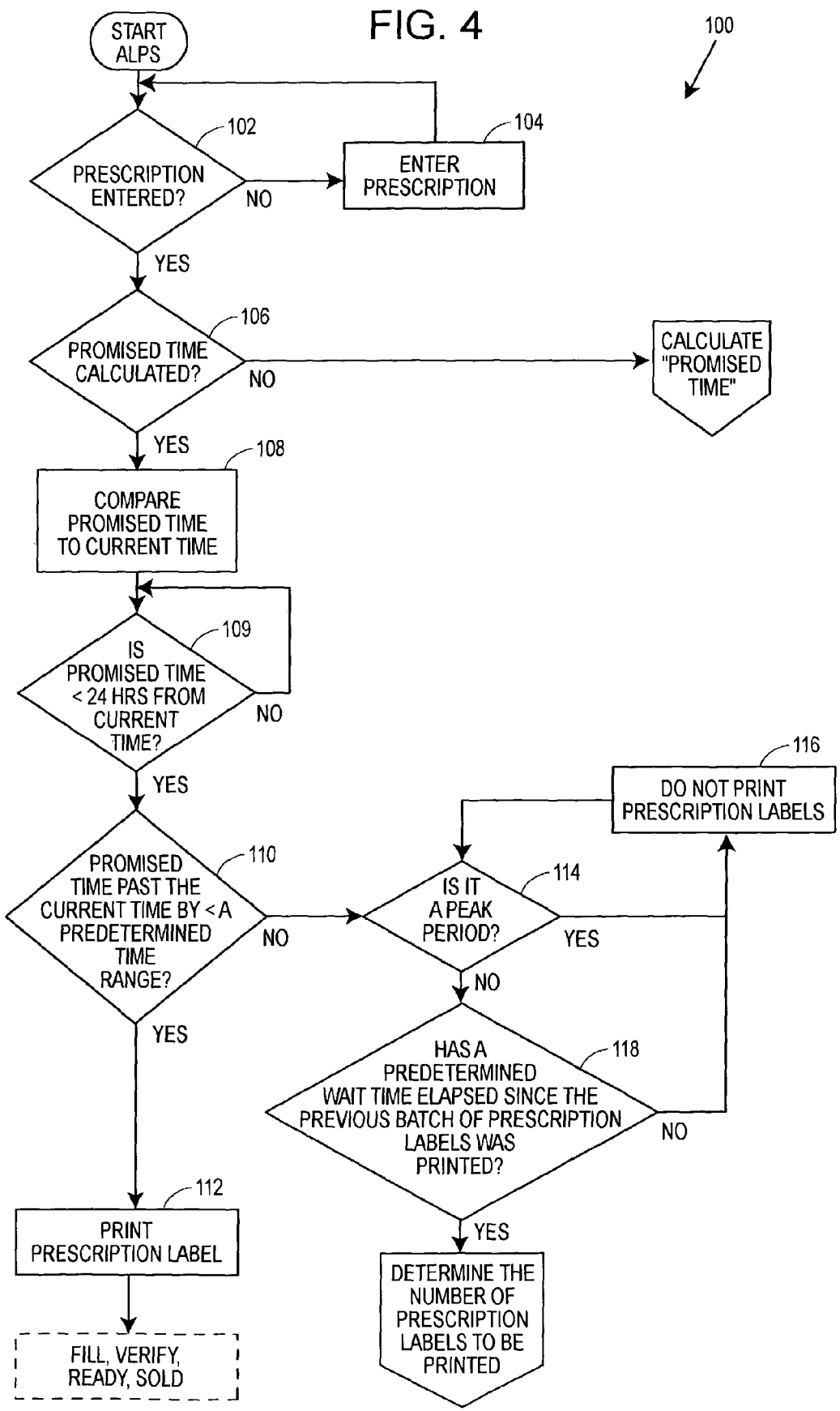
FIGS. 4, 5, and 6 are three parts of a flowchart of a main routine that may be performed during operation of an automated label printing system.
Figure 5:
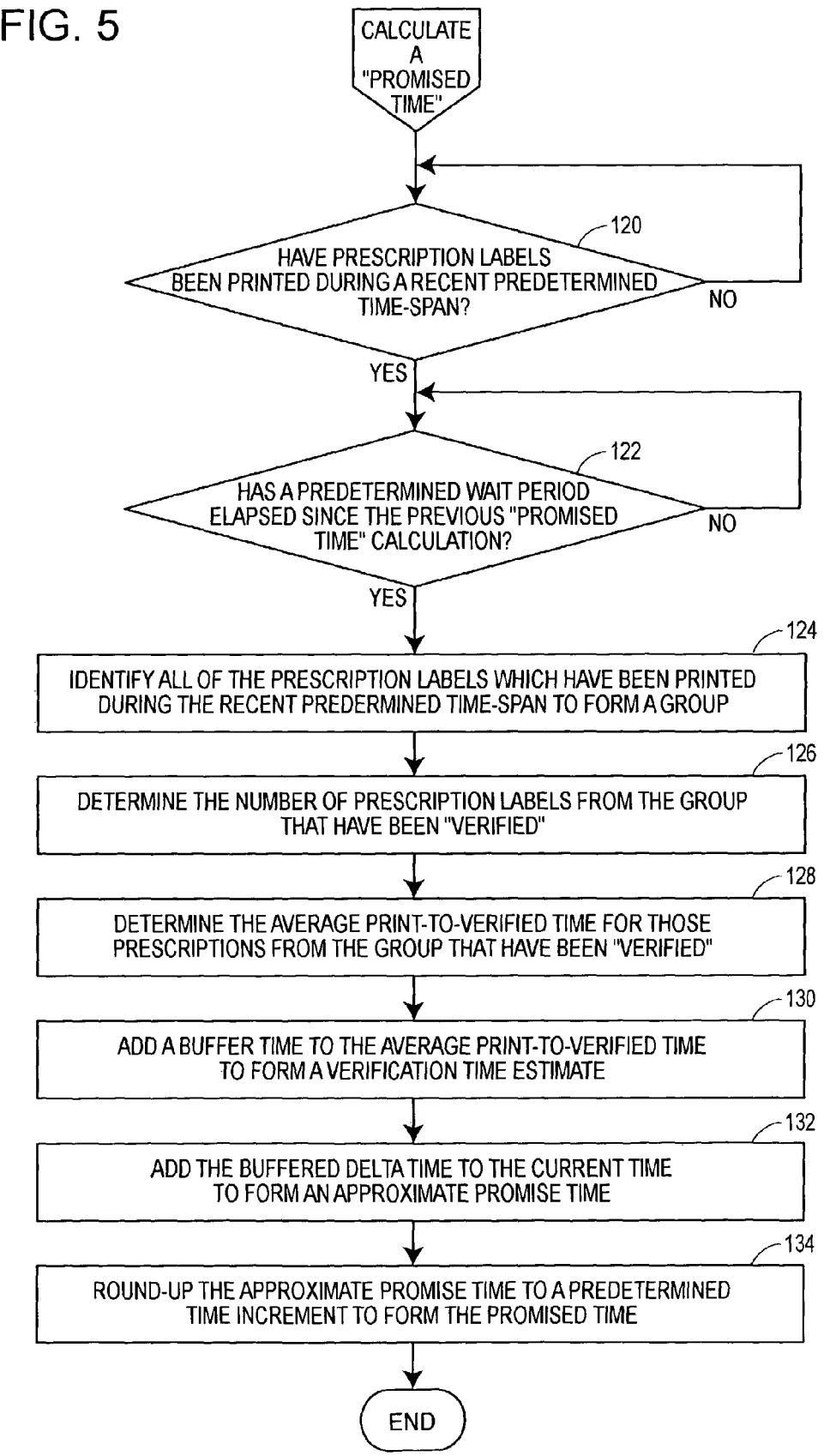
Figure 6:
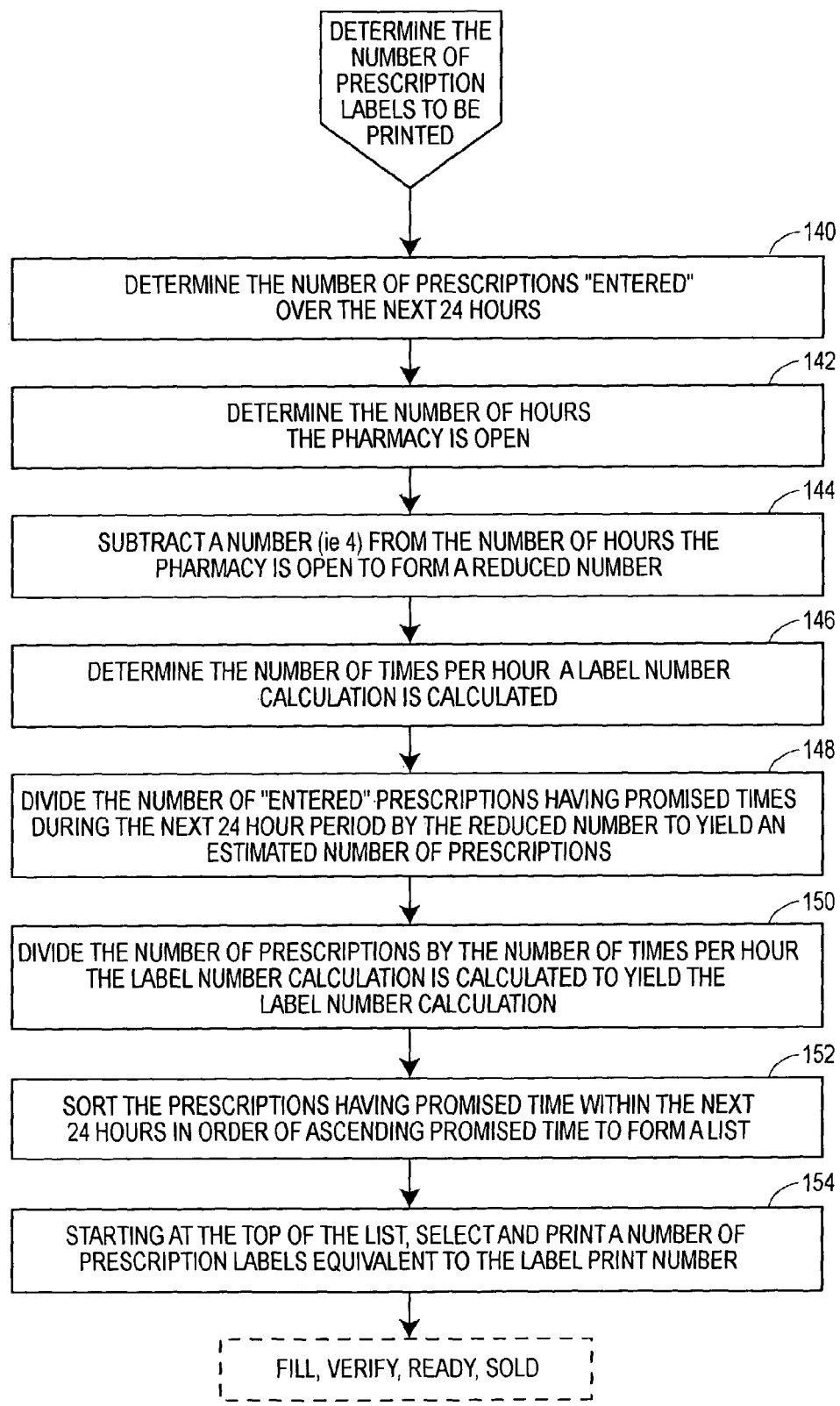

FIGS. 4, 5, and 6 illustrate some of the steps of an operating routine or subroutine 100 that may be stored in the memory of the controller 18. The routine 100 may be performed during operation of the ALPS 26 and may continue to run during normal operating hours of the pharmacy. While executing the routine 100, the controller 18 may cause an adjustable amount of prescription labels to be printed to ensure a steady organized flow of the overall prescription workflow 52. The adjustment to the label printing amount is predicated on a number of factors, which primarily includes whether the pharmacy is experiencing a peak operation period.

As previously described, the order in which prescription labels are printed by the ALPS 26 determines the order in which the prescriptions are subsequently filled and verified with the assumption that the drugs are available. The label print order is based on a number of factors including, but not limited to, promised times for prescription delivery to patients, the peak prescription workflow period for that particular pharmacy, pharmacy operation hours, the number of batches of prescription labels printed per hour, and the number of prescriptions labels printed per batch. Thus, the ALPS 26 provides a fully automated label scheduling and printing system that translates into steady pharmacy workflow throughout the day for a pharmacy with traditional hours of operation. The ALPS 26 also provides a fully automated label scheduling and printing system that translates into an adjustable pharmacy workflow throughout a 24-hour time period required for a pharmacy that is opened 24 hours.

Referring to FIG. 4, the routine 100 begins operation at a block 102 to determine if the prescription order 8 has been entered into the prescription workflow 52. For example, the prescription order 8 has been entered into the prescription workflow 52 when the prescription order 8 has been assigned an "Entered" status on the pharmacy work queue. Otherwise, the prescription order 8 is entered into the prescription workflow 52 at a block 104. After the prescription order 8 is entered into the prescription workflow 52, the controller 18 at a block 106 may determine whether a promised time has been calculated and assigned to the prescription 9 associated with the prescription order 8 (e.g., the prescription 9 will be ready in 20 minutes). If the promised time has been calculated and assigned, the promised time is compared with the current time at a block 108. If the controller 18 determines that the promised time falls within the next 24-hour time period at a block 109, the prescription 9 is considered for printing (i.e., a prescription label and instructions for the prescription 9 are printed by the printer 27). If the promised time is outside of the 24-hour time period, the prescription 9 is not considered for printing.

After the promised time of the prescription 9 is determined to fall within the 24-hour time period, the controller 18 at a block 110 may determine whether the promise time is past the current time by less than a predetermined time range (e.g., the promised time for delivery of the prescription 9 is within the next 30 minutes). If the promised time is past the current time (i.e., delivery of the prescription 9 is due shortly), the controller 18 at a block 112 directs the ALPS 26 to print the prescription label for the prescription 9 in the next printing of a batch of prescription labels. Thus, the prescription label for the prescription 9 would be among the next batch of printed prescription labels printed by the printer 27.

Referring back to the block 110, if the controller 18 determines that the promised time is past the current time by more than the predetermined time range (e.g., the promised time for delivery of the prescription 9 is beyond the next 30 minute window), the controller 18 at a block 114 may determine if the current time falls within a peak prescription workflow time period. If the controller 18 at a block 116 determines that the current time is within the peak prescription workflow period, the prescription label for the prescription 9 will not be printed in the next printing batch of prescription labels. For example, if the peak prescription workflow period is between the hours of 4 p.m. and 7 p.m. and a prescription 9 has a promised time past the current time by more than the predetermined time range, the prescription label for the prescription 9 will not be considered for printing until the peak period has elapsed.

As soon as the peak period elapses, prescriptions having promise times past the current time by more than the predetermined time range will be considered for label printing. Next, the controller 18 at a block 118 may determine whether a predetermined wait time (e.g., 15 minutes) has elapsed since the previous batch of printed labels. If the predetermined wait time has not elapsed, the controller 18 proceeds to the block 116 and the prescription label for the prescription 9 will not be considered for printing. However, if the predetermined wait time has elapsed, the controller 18 may consider printing the prescription label for the prescription 9 in the next batch of printed labels. The decision to print the prescription label for the prescription 9 in the next batch of printed labels is based on a number of prescription labels to be printed in that next print batch.

Persons of ordinary skill in the art will readily appreciate that other methods of performing the routine 100 are contemplated. For example, some of the blocks may be changed, the order of execution of the blocks may be changed, and/or some of the blocks described may be optional. In addition, the routine 100 may include blocks that group prescriptions associated with the same primary phone number (indicating the same patient or patients living in the same household) so that the prescription labels for the group prescriptions may be printed in the same batch of prescription labels. In addition to enhancing pharmacy staff efficiency, grouping prescriptions in this way may reduce the number of trips to the pharmacy by a patient to accept delivery of the prescriptions.

Returning back to the block 106 (shown in FIG. 4), FIG. 5 illustrates the steps to calculate the promised time of the prescription 9 entered into the prescription workflow 52 in further detail. Referring to FIG. 5, the controller 18 at a block 106 may determine that the entered prescription has not been assigned a promised time. Accordingly, the controller 18 at a block 120 may determine if one or more prescription labels have been printed during a recent predetermined time span (e.g., previous 90 minutes).

If the controller 18 determines that the prescription label(s) were not printed during the recent predetermined time span, the controller 18 proceeds to the block 120 until the prescription label(s) were printed during the recent predetermined time span. If the controller 18 determines that the prescription label(s) were printed during the recent predetermined time span, the controller 18 at a block 122 may determine if a predetermined wait period has elapsed since a previous calculation of a promised time. For example, the controller 18 may calculate prescription delivery promised times every 5 minutes to ensure that the promised times reflect up-to-date calculation variables (e.g., the number of prescriptions requested, and the number of patients waiting in the pharmacy). If the predetermined wait period has elapsed, the controller 18 at a block 124 may identify the prescription labels printed during the recent predetermined time span (e.g., 90 minutes) (hereinafter referred to as a "group of labels").

Next, the controller 18 at a block 126 may identify those prescription labels from the group of labels that have been verified by a pharmacist and assigned a "verified" status. As previously described, a prescription label is assigned a "verified" status upon completion of a verification process by the pharmacist. The verification process includes, but is not limited to, scanning a prescription label bar code on the prescription label to cause a screen of prescription/patient information to be display on the user interface 36, inspecting the displayed prescription/patient information, and acknowledging the correctness of the displayed prescription/patient information such as contents of the prescription.

Based on the number of verified labels of the group of labels, the controller 18 at a block 128 may determine an average print-to-verified time (i.e., the average time between printing the prescription labels and verifying the prescription labels during recent pharmacy conditions). At a block 130, a "verification time estimate" is calculated by adding a buffer time period (e.g., 3 minutes) to the average print-to-verified time to allow for miscellaneous tasks. The buffer time is selected to include a time period for entering the prescription plus a time period to prepare the prescription for sale after it has been verified. The verification time estimate is added to the current time to form an "approximate promise time" at a block 132. Finally, the approximate promise time is converted to the "prescription promised time" at a block 134 by rounding up the approximate promised time to a new time, wherein the new time represents the beginning of a next set of predetermined time increments. For example, rounding up an approximate promise time of 3:16 pm to a new time of 3:20 p.m., wherein the new time of 3:20 marks the beginning of the next five-minute increment of a set of 12 five-minute increments for each hour. Based on recent past data, the resulting prescription promised time is used by the controller 18 to determine which prescription labels are to be printed in the immediate future.

FIG. 6 illustrates the steps to determine the number of prescription labels to be printed (hereinafter referred to as a "label print number calculation"). Referring to the block 118 (shown in FIG. 4), the prescription labels to be printed are associated with prescriptions having a promised time past the current time by more than the predetermined time range. Referring to FIG. 6, the controller 18 performs a label print number calculation based on a number of factors such as, but not limited to, the number of prescriptions in the prescription workflow, the pharmacy hours of operation, and the number of times per hour the label print number calculation is performed.

If the controller 18 at a block 140 determines that the predetermined wait time (e.g., 15 minutes) has elapsed subsequent to the previous prescription label print batch, the controller 18 may determine the number of prescriptions having (1) a promised time during the next 24-hour time period and (2) an "entered" status. Next, the controller 18 at a block 142 may determine the hours of operation of the pharmacy (i.e., when the pharmacy is open). At a block 144, the controller 18 may subtract a preselected number of hours from the number of hours that the pharmacy is open to form a "reduced number". For example, if the pharmacy is opened from 7 a.m. to 7 p.m. (i.e., twelve hours), the controller 18 at the block 144 may reduce that number by a preselected number such as four to reduce the hours of operation to eight hours, which is the number of hours that the pharmacy is open. The controller 18 at a block 146 may determine the number of times the label print number calculation is performed in an hour.

At a block 148, the number of prescriptions having (1) a promised time during the next 24-hour time period and (2) the "entered" status is divided by the reduced number to yield an estimated number of prescriptions per hour. The estimated number of prescriptions per hour is then divided by the number of times the label print number calculation is performed in an hour at a block 150. The resulting number (i.e., the "label print number") represents the number of labels to be printed in the next batch of printed prescription labels.

Next, the controller 18 at a block 152 may sort the prescriptions having (1) a promised time during the next 24-hour time period and (2) the "entered" status in ascending order of their prescription promised time. Finally, a number of prescription labels equivalent to the label print number is printed in ascending order of their associated prescription promised times at a block 154. In addition, prescriptions having (1) promised times during the next 24-hour time period, (2) the "entered" status, and (3) the same primary phone number may have their prescription labels printed in the same batch of prescription labels.

Persons of ordinary skill in the art will readily appreciate that other methods of performing label print number calculation are contemplated. For example, some of the blocks may be changed, the order of execution of the blocks may be changed, and/or some of the blocks described may be optional.

As will be appreciated by persons of ordinary skill in the art, the particular arrangement of the sections of the prescription label along with numerous variations may be created. The prescription label for the prescription 9 may be a two-sided prescription label having a front side and a back side printed by the printer 27. The front side may include a bar code used by the pharmacist to verify the prescription/patient information. The front side may also include, but is not limited to, the patient's primary phone number, the patient's address, the prescription's promised time of delivery to the patient, prescription instructions and warning labels, and general consumer drug information.

The back side may include a copy of some of the information displayed on the front side including the bar code, and the patient's primary phone number. In addition, a pharmacy or store logo may be included on the back side. Additional useful information such as, but not limited to, the prescription drug name, a common drug use comment, prescription drug usage information, a list of cautions, a list of possible side effects, as well as any additional notes may be included by the pharmacy. Thus, the front side and back side of the two-sided prescription label may contain the necessary information for tracking, verifying, and filling the prescription as well as provide a way to transmit pertinent information to the patient. Additional details on the two-sided prescription label may be found in the patent application entitled "Duplex Pharmacy Label and Method," having U.S. Ser. No. 10/022,583, filed on Dec. 17, 2001, and the disclosure of which is incorporated herein by reference.

As previously mentioned, the timing of the printing of the two-sided prescription label is determined by the ALSP 26. Therefore, the ALPS 26 may provide automatic printing of the optimal number of prescription labels based on the "promised times" and the current number of prescriptions to be printed during the next 24-hour time period. Further, the ALPS 26 may enable a steady flow of prescription fills based upon the printing time of the prescription labels.

Operation of the Exception Manager

As discussed in connection with FIG. 2, a prescription order 8 is received and entered into the prescription workflow 52. Accordingly, automatic printing of a prescription label for the prescription 9 associated with the prescription order 8 is directed by the ALPS 26 based on a number of factors as discussed above. Optimally, the order in which the prescription label for the prescription 9 is printed by the ALPS 26 determines the order in which the prescription 9 is filled and verified. However, exceptions (i.e., unresolved tasks associated with filling and verifying the prescription) may prevent the prescription 9 from being timely filled, verified, and/or delivered to the patient. For example, the exceptions include a need to call a medical doctor to renew the patient's prescription, to await a call back from the medical doctor, or to re-call the medical doctor. The exceptions may also include verifying the patient's insurance coverage, which may require a call to or from a third party insurance provider. Further, the exceptions may include a need to research a possible drug interaction between the prescription ordered and other prescriptions that the patient is currently taking. Other exceptions may involve a requirement to check possible generic drug substitutes or a situation where only a portion of the prescription is available for immediate dispensing to the patient. In addition, there are numerous other possible exceptions that may prevent the prescription from being timely filled, verified, and/or delivered to the patient, and which may fall into a catch-all category hereinafter referred to as a miscellaneous category.

One method for noting an exception(s) associated with a prescription is to use short identifiers such as acronyms or abbreviations. For example, a list of exceptions with their associated abbreviations is shown in Table 1.

TABLE 1

| Type of Exception | Identifier |
| --- | --- |
| Call medical Dr. | CMD |
| Dr. will call back | WCB |
| Re-call medical Dr. | RMD |

TABLE 1-continued

| Type of Exception | Identifier |
|---|---|
| Third-party insurance rejection | TPR |
| Prescription is out of stock | OOS |
| Generic substitute is available | GEN |
| Prescription may only be partially filled | PFL |
| Miscellaneous | MSC |
| Drug utilization review for drug interaction needs to be completed | DUR |

Of course, manual tracking of the exception(s) associated with a prescription consumes a substantial amount of the pharmacy staff's time. The exception manager 28 (FIG. 2) operates to reduce the amount of pharmacy staff time required to track the exceptions to their conclusion. After an exception has been attached to a prescription, the exception manager 28 allows automatic priority ranking and identifying of prescription/exceptions to be resolved prior to prescription delivery to the patient. The exception may be attached to the prescription either manually by the pharmacy staff as in the case of a miscellaneous exception or automatically as in the case where a shortage of a particular drug has been identified at the step of entering the prescription order into the prescription workflow 52 (e.g., identified as a zero stock status within the inventory of the pharmacy).

Because resolution of an exception becomes more critical as the promised time draws near, the exception manager 28 is configured to allow a pharmacy staff member to quickly identify and resolve prescription/exceptions that have promised times within a specified time duration (e.g., within 75 minutes of the promised time). Once identified as a prescription/exception having a promised time with the specified time duration, the prescription is termed a "priority exception."

Access to information associated with the priority exceptions may be accomplished via a user interface such as the user interface 36 shown in FIG. 1. When prompted by a pharmacy staff member via executing a key stroke on a workstation keyboard, the user interface 36 may display one or more graphics displaying information associated with the priority exception. The graphic may also include the steps necessary to resolve the priority exception. In addition, the information associated with the priority exception shown in the graphic display may be posted on the user interface 36 in priority order of the nearest promised time. For example, a priority exception that is closest to its promised time will be displayed first, followed by a priority exception that is second closest to its promised time, and so on.

Figure 7:
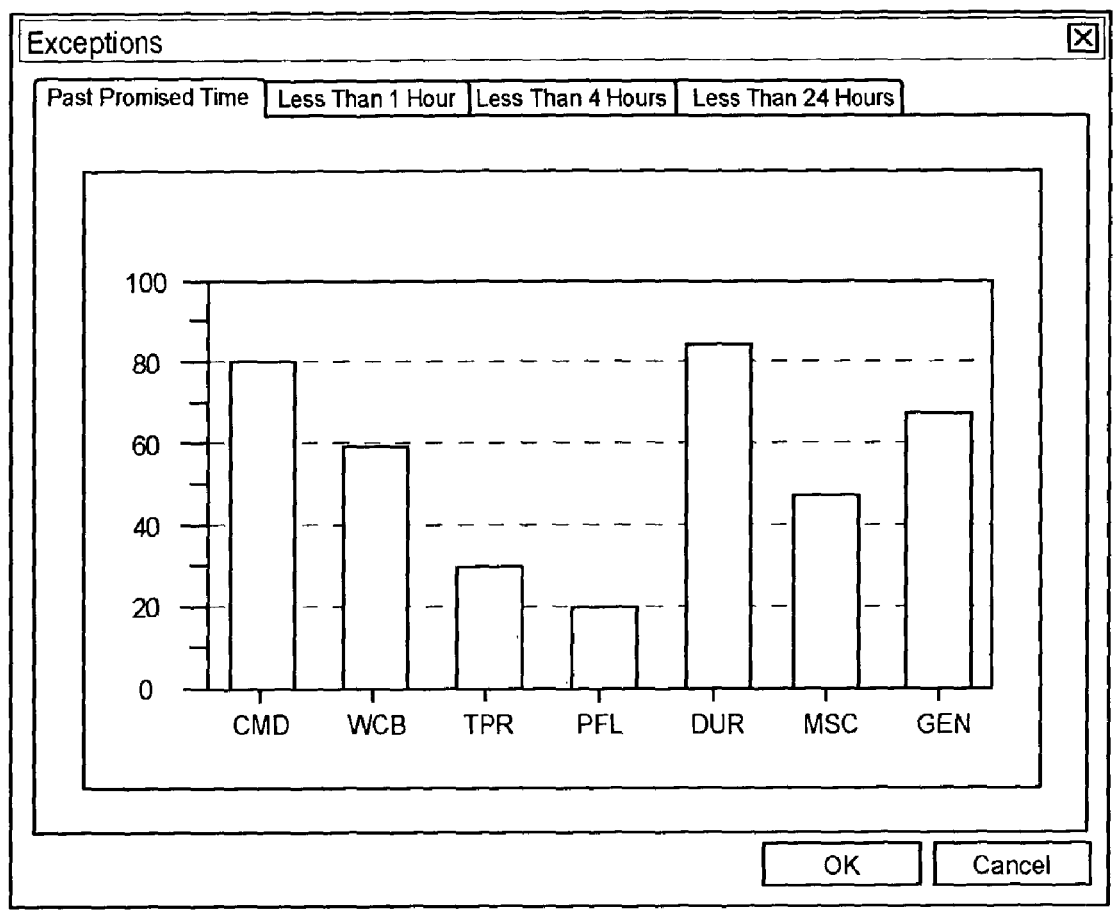

The user interface 36 may be used to post prescription/exceptions including priority exceptions. That is, the user interface 36 may provide, but not limited to, a bar graph showing the types and numbers of prescription/exceptions, a bar graph showing the types and numbers of priority exceptions that have promised times in less than an hour, a bar graph showing the types and numbers of prescription/exceptions that have promised times in less than four hours, and a bar graph showing the types and numbers of prescription/exceptions that have promised times in less than 24 hours. Referring to FIG. 7, for example, the user interface 36 may provide a bar graph showing the types and numbers of prescription/exceptions that are past their promised time.

Further, the user interface 36 may provide a graphic display to show information associated with a priority exception. Referring to FIG. 8, for example, the graphic display 300 may show information associated with a prescription having the CMD (call medical doctor) exception. The exemplary graphic display 300 may include, but is not limited to, patient contact information 302, the promised time 304, a prescription identifier number 306, the exception type 308, and resolution instructions 310 to the pharmacy staff member providing the step(s) necessary to resolve the exception. The user interface 36 may provide a graphic display to show information associated with other priority exceptions such as, but not limited to, the TPR exception, the MSC exception, the GEN exception, and the DUR exception.

As noted above, priority exceptions past their promised time are referred to as "priority prescriptions." Priority prescriptions also include those prescriptions past their promised time that have been entered into the prescription workflow but do not have printed labels. Further, priority prescriptions may also include those prescriptions past their promised time that have had prescription labels printed and have been filled but have not been verified.

In addition to providing priority and status to a pharmacy staff member, the graphic displays of priority exceptions represented by FIGS. 7 and 8 are configured to prompt the pharmacy staff member viewing the display to call and notify the patient of the status of his/her prescription. Thus, the pharmacy staff member may be able to prioritize tasks associated with the prescription workflow 52 efficiently to resolve prescription exceptions and to reduce inconvenience to the patient.

Figure 9:
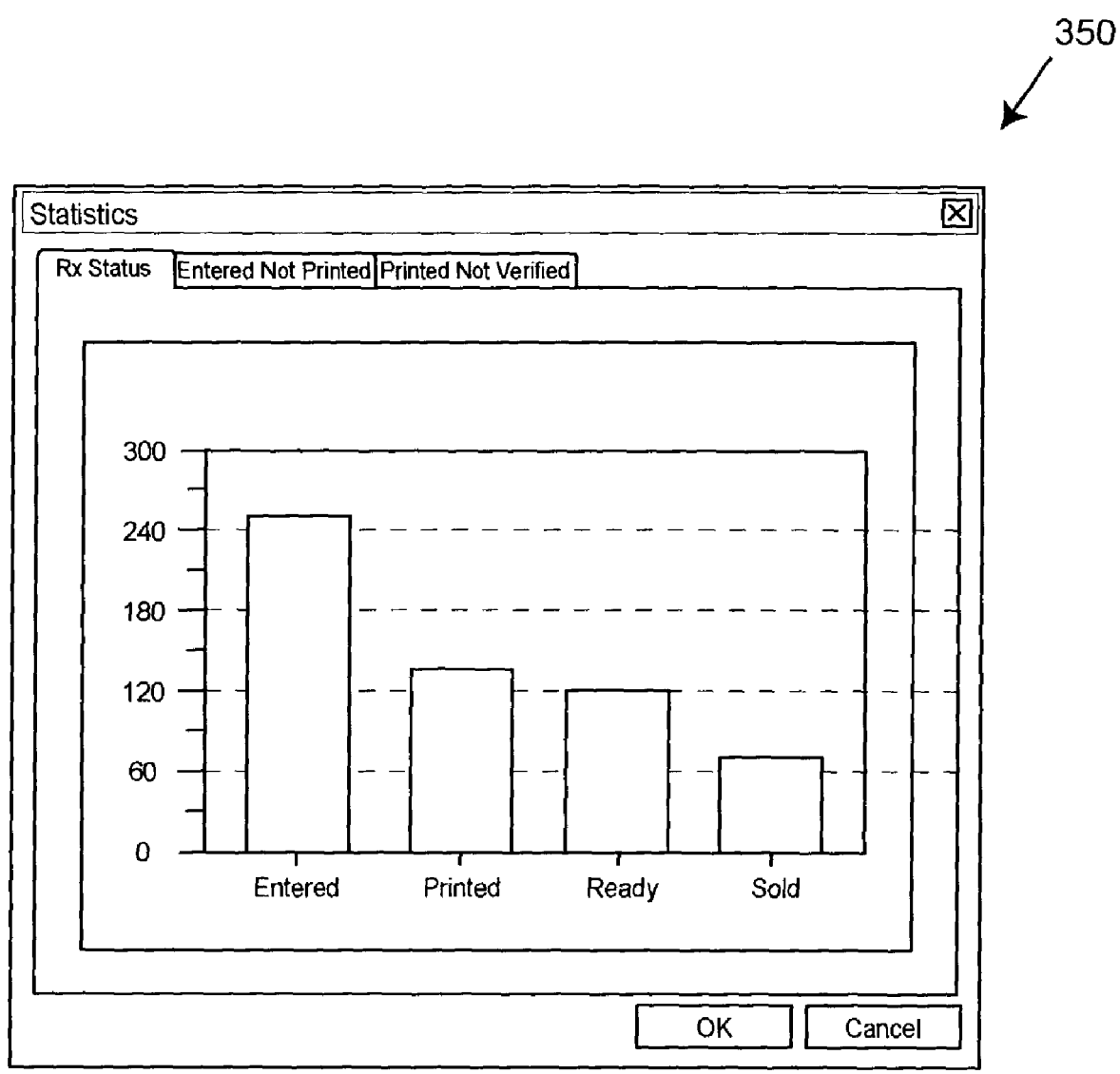
FIGS. 9, 10, and 11 are graphic displays to show statistics of prescription orders.
Figure 10:
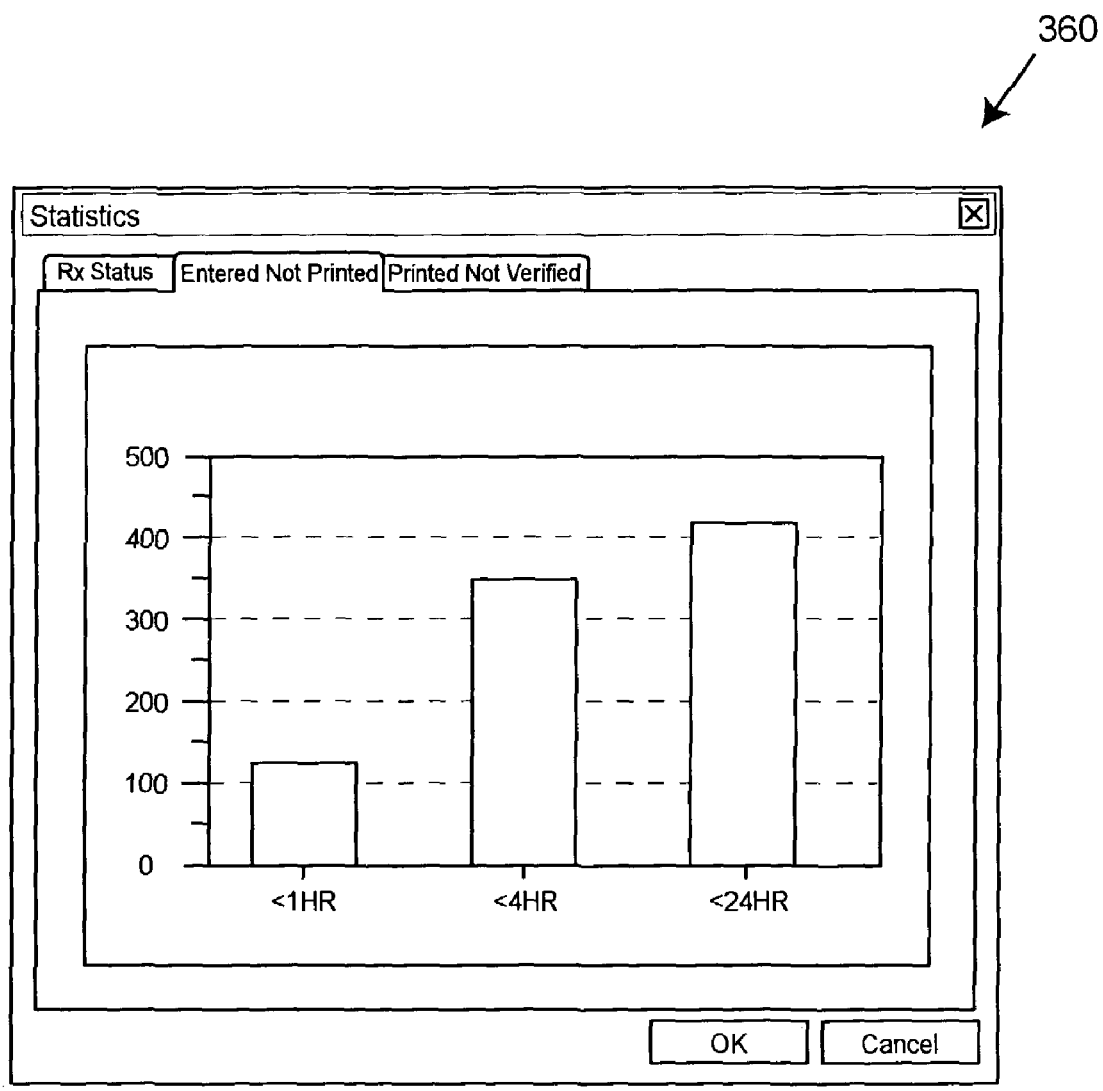
Figure 11:
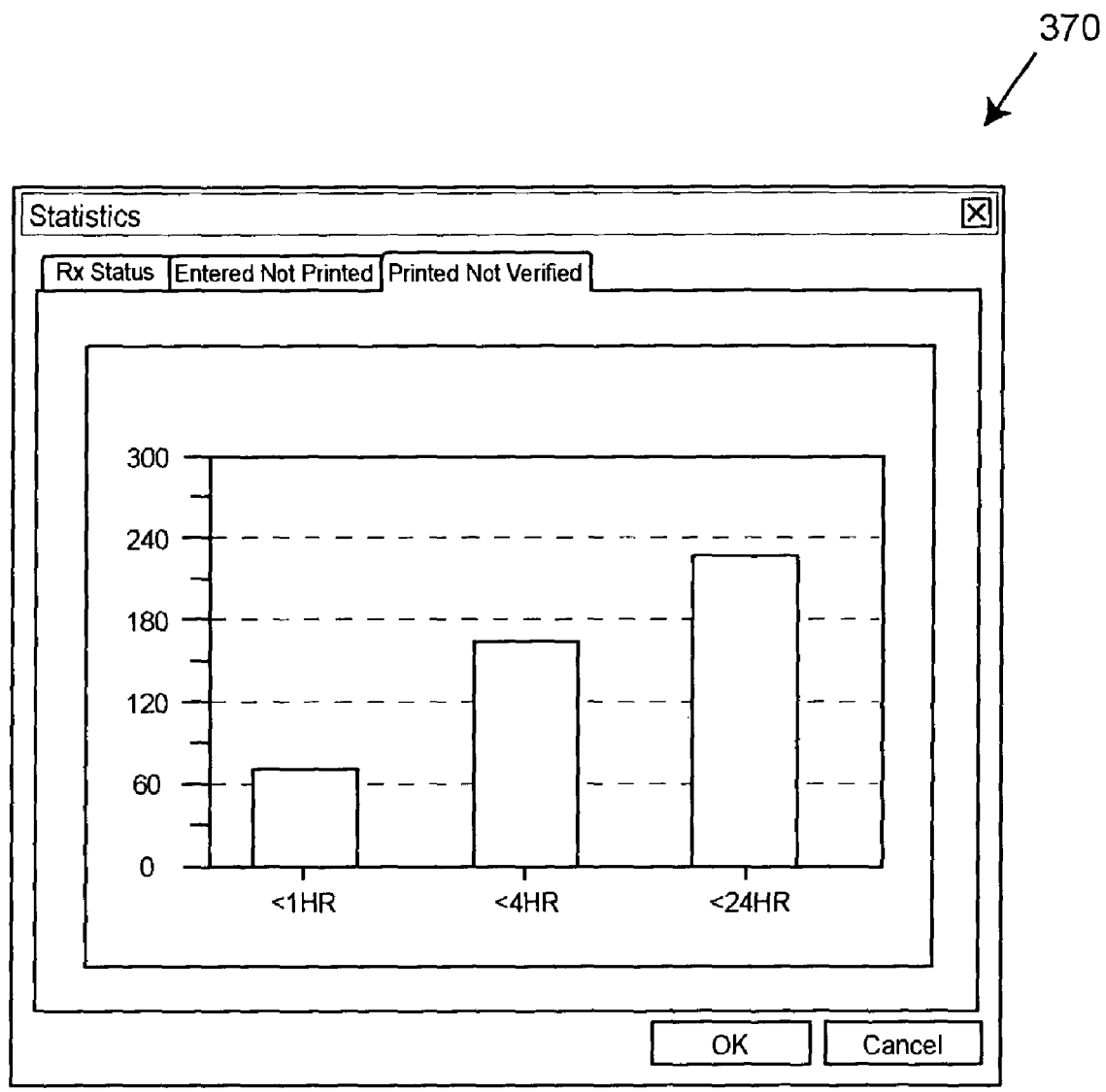

Another type of graphic display, hereinafter referred to as a "statistics display" is provided by the exception manager 28 to present a quick status of all prescription orders in the prescription workflow to the pharmacy staff (e.g., outstanding prescription orders). For example, a graphic display 350 shown in FIG. 9 may provide the number of prescription orders that have entered into the prescription workflow 52, the number of prescription labels printed by the printer 27, the number of prescriptions ready for patient pick-up, and the number of prescriptions sold. In another example, selection of an "Entered Not Printed" tab may provide a graphic display 360 as shown in FIG. 10. The graphic display 360 may provide a status of a number of prescription orders that have been entered into the prescription workflow 52 but do not have printed prescription labels for the prescriptions. Thus, those prescriptions have not been filled or verified (i.e., Entered Not Printed). The prescriptions may be grouped based on their promised times (e.g., prescriptions having promised times in less than an hour, prescriptions having promised times in less than four hours, and prescriptions having promised times in less than 24 hours). Alternatively, selection of a "Printed Not Verified" tab may provide a graphic display 370 as shown in FIG. 11. The graphic display 370 may provide the number of prescription orders that have been entered into the prescription workflow 52 and the prescriptions have been filled but have not yet been verified. Thus, the statistics of the graphic displays 350, 360, 370 illustrated by FIGS. 9-11 may provide another tool for pharmacy staff members to prioritize tasks associated with the prescription workflow 52.

Therefore, the exception manager 28 may automatically "serve up" the highest priority (based on the promised time) prescription with an exception to the pharmacy staff members to allow resolution of the exception or to prompt notification to the patient as to when the prescription may be ready for pick-up.

Operation of the Rx Ready Manager

As described above in FIG. 2, the exception manager 28 provides graphic displays showing prescription/exception information including text instructions that notify the pharmacy staff member of the steps necessary to resolve the exception and to move the prescription order along in the prescription workflow. For example, the instructions may prompt a pharmacy staff member to call and notify the patient of the status of his/her prescription. Although the pharmacy staff member is provided with instructions to resolve the exception to save valuable staff time, the pharmacy staff member is required to perform an additional task. That is, the pharmacy staff member must manually place a phone call to the patient to notify him/her of the not-ready status of the prescription.

The addition of the Rx-ready manager 30 as shown in FIG. 2 enables automatic notification to a patient when a prescription will not be ready for pick-up at the promised time. The Rx-ready manager 30 is also configured to automatically notify patients, who have been previously notified of the not-ready status of his/her prescription, that his/her prescription is now ready for pick-up. The workload of the pharmacy staff members may decrease by automating the not-ready and now-ready phone calls, which were previously made by manually calling the patients. In addition, the number of patients served may increase by providing the not-ready and now-ready phone calls as needed rather than being part of the standard procedure. Prescriptions that are candidates for the Rx-ready manager 30 may include, but are not limited to, (1) prescriptions with exceptions that were not resolved prior to the promised time, (2) prescriptions that have printed labels and have been filled but have not been verified by the promised time, and (3) prescriptions of prescription orders that have been entered into the system but do not have printed labels by the promised time. Both not-ready and now-ready notification may occur in a number of ways such as, but not limited to, an automated telephone call with a prerecorded voice message to the patient, a page to the patient, a short message page to the patient, and e-mail.

Figure 12:
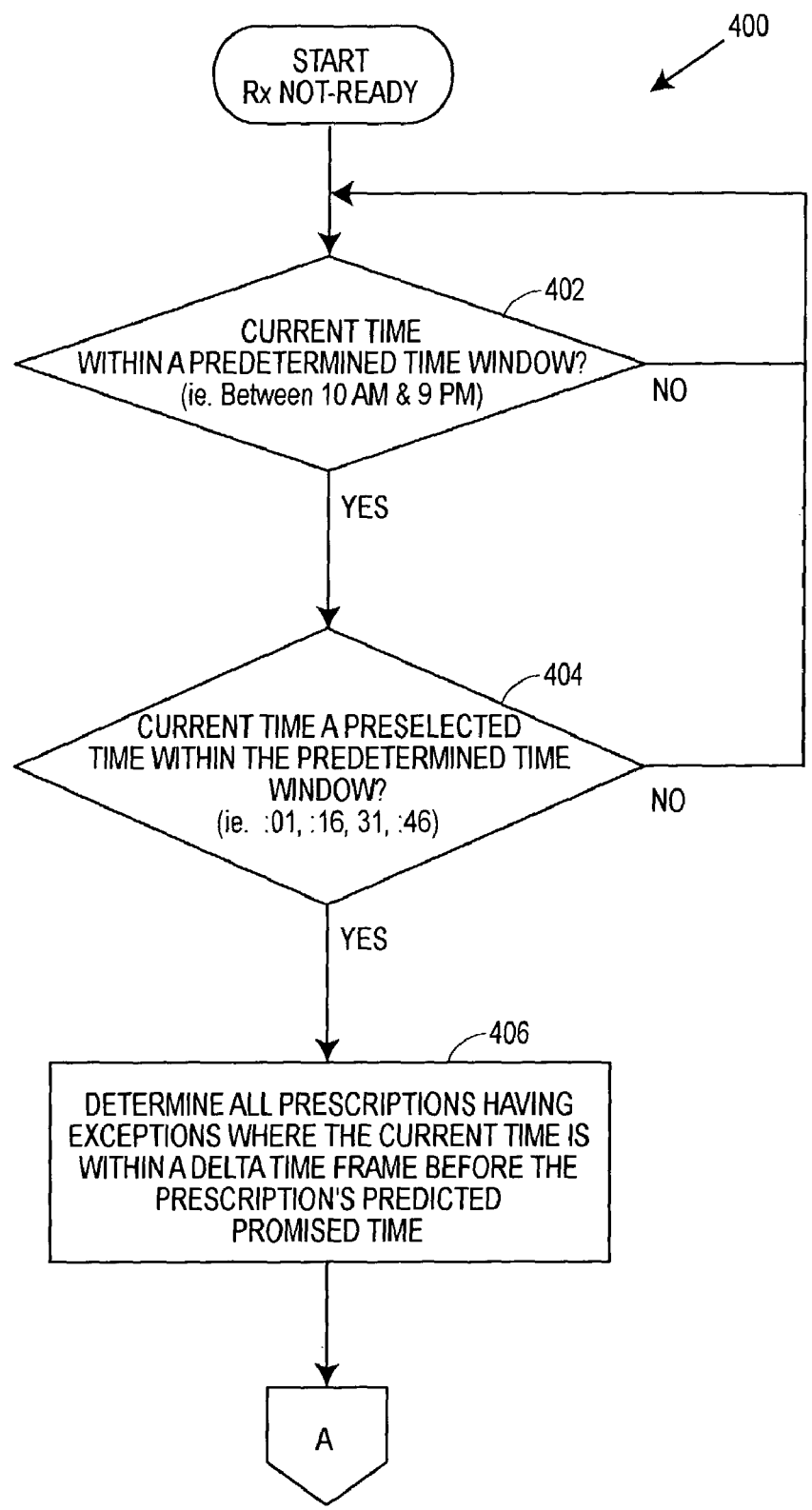
FIGS. 12 and 13 are two parts of a flowchart of a main routine that may be performed during operation of an Rx-ready manager.
Figure 13:
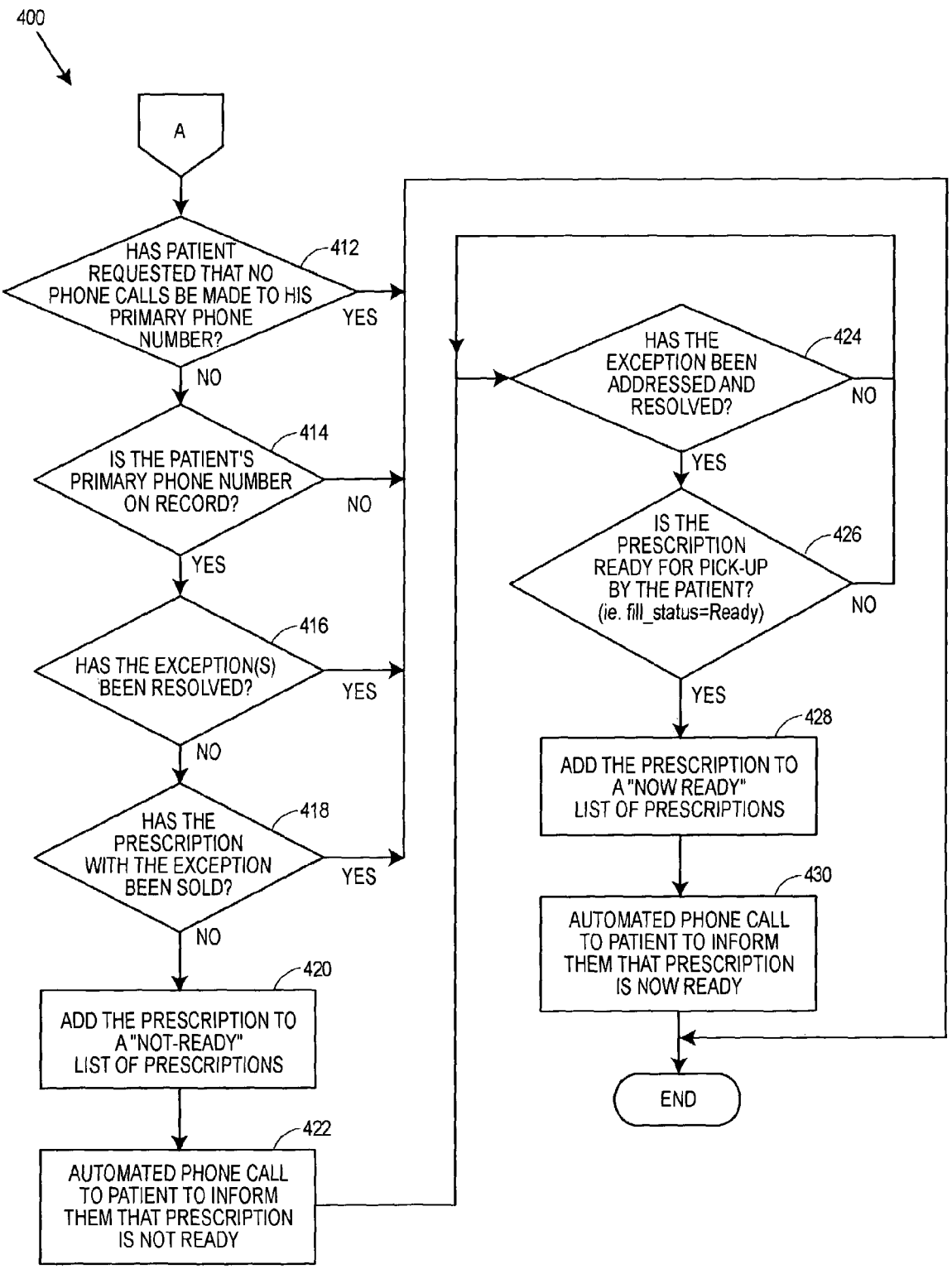

FIGS. 12 and 13 illustrate some of the steps of an operating routine or subroutine 400 that may be stored in the memory of the controller 18. The routine 400 may be performed during operation of the Rx-ready manager 30 and may continue to run during normal operating hours of the pharmacy. While executing the routine 400, the controller 18 may cause automated phone calls to be made to patients to inform them that their prescription is either not ready or ready. Accordingly, execution of the routine 400 may reduce the workload of the pharmacy staff members by replacing inconsistent, manual prescription not-ready and prescription ready phone calls with consistent, automatic phone calls to the patient. Thus, the quality of customer service provided to the patient may increase.

The routine 400 begins at a block 402 where the controller 18 may determine whether the current time is within a predetermined time window, (e.g., a window of time between 10 a.m. and 9 p.m). If the current time is not within the predetermined time window, the controller 18 may not proceed to the next step of the routine 400. However, if the current time is within a predetermined time window, the controller 18 at a block 404 may determine whether the current time is one of a number of preselected times within the predetermined time window. The preselected times within the predetermined time window may include, for example, the times of 10:01 a.m., 10:16 a.m., 10:31 a.m., 10:46 a.m., 11:01 a.m., and so on until the predetermined time window has elapsed. If the current time is not one of the preselected times within the predetermined time window, the controller 18 may not proceed to the next step of the routine 400.

If the current time is one of the preselected times within the predetermined time window, the controller 18 may conduct a systematic search for prescription/exceptions that may require a phone call to the patient (e.g., a not-ready phone call or a now-ready phone call). The controller 18 at a block 406 may determine the prescription/exceptions with the current time being within a delta time-frame before the promised time of the prescription. The delta time-frame may be any suitable time-frame that is preselected to allow the pharmacy staff ample time to resolve the exception(s) while at the same time, to enable notification to the patient in a timely manner. For example, if 60 minutes is selected as the delta time-frame, a prescription/exception having a promised time of 45 minutes may be determined by the controller 18 as being a prescription/exception that is within a preselected delta time-frame before the promised time of the prescription.

Referring to FIG. 13, the controller 18 may determine whether the patient has requested that no phone calls be made to his/her primary phone number by the pharmacy staff members for each prescription/exception determined to be within the delta time-frame before the promised time (As previously mentioned, the pharmacy customer database stores information regarding the patient's preferences). If the patient has requested that no phone calls be made then all prescriptions associated with that patient may be exempt from the Rx-ready manager 30. If the patient has not made a no-phone-calls request, the controller 18 at a block 414 may determine whether the patient's primary phone number is on record. If the patient's primary phone number is not on record, then all prescriptions associated with that patient may be exempt from the Rx-ready manager 30 unless the patient reveals his/her phone number.

Next, the controller 18 at a block 416 may determine whether the exception associated with the prescription has been resolved or can be immediately resolved. If the exception associated with the prescription has been resolved or can be immediately resolved, the prescription is not a candidate for the Rx-ready manager 30. If the exception associated with the prescription has not been resolved or cannot be immediately resolved, the controller 18 at a block 418 may determine whether the prescription has been sold or is ready for delivery to the patient. This type of situation may occur, for example, when a prescription with an MSC (miscellaneous) exception created by a pharmacy staff member is sold to the patient despite the exception or when the resolution status of the MSC exception may not have been properly logged into the prescription workflow. If the prescription/exception has been sold or is ready for delivery to the patient, the prescription is not a candidate for the Rx-ready manager 30. If the prescription has not been sold or is not ready for delivery to the patient then the prescription may be added to a not-ready list of prescriptions that are (1) not ready for patient pick-up and (2) have promised times that are within the preselected delta time frame at a block 420. Finally, the controller 18 at a block 422 may cause automated phone calls to be placed to the patients having prescriptions on the not-ready list to inform them that their prescription is "not ready." If the not-ready phone call is not properly received, the controller 18 may cause additional phone calls to be placed to the patient's primary phone number until receipt of the not-ready phone call is acknowledged either by an answering machine or a person at the location having the primary phone number, or until a predetermined number of attempts have been made.

After receipt of the not-ready phone call is acknowledged, the controller 18 at a block 424 may determine whether the exception associated with the prescription has been resolved. If the exception associated with the prescription has not been resolved, the prescription is held in the prescription workflow 52. However, if the exception associated with the prescription has been resolved, the controller 18 at a block 426 may determine whether the prescription is ready for delivery to the patient. If the prescription is not ready for delivery to the patient, the prescription is held in the prescription workflow 52. However, if the prescription is ready for delivery to the patient (e.g., has a fill_status=Ready) then at a block 428, the prescription is added to a now-ready list of prescriptions that (1) have had previous automated not-ready phone calls made to the patient, and (2) are currently ready for delivery to the patient. Finally, at a block 430, an automated phone call or other notification is placed to the patients having prescriptions on the now-ready list to inform them that their prescription is "now ready." If the now-ready phone call is not received, the controller 18 may cause additional phone calls to be placed to the patient's primary phone number either until receipt of the now-ready phone call is acknowledged either by an answering machine or a person at the location having the primary phone number or until a predetermined number of attempts have been made.

It should be noted that the routine 400 may also include steps to form a group of now-ready and not-ready prescriptions associated with the same primary phone number. In that case, the controller 18 may not cause the automated now-ready phone call to be placed to the patient until all of the prescriptions in the group have attained a "now-ready" status. Grouping prescriptions this way may reduce the number of trips to the pharmacy by a patient to accept delivery of the prescriptions and may reduce the overall number of phone calls to the patient.

Dashboard Display

As mentioned above, pharmacy staff efficiency and customer satisfaction are at their highest levels when the prescription workflow is timely and patient information is made available to the pharmacy staff in an easy to understand format. A summary status bar (i.e., referred to as a "dashboard" 40, 42 displayed on the user interfaces 36, 38 as described above) may provide an easy-to-read, up-to-date visual graphic display of data associated with the pharmacy, the prescription workflow 52, and the performance of the pharmacy staff.

Figure 14:
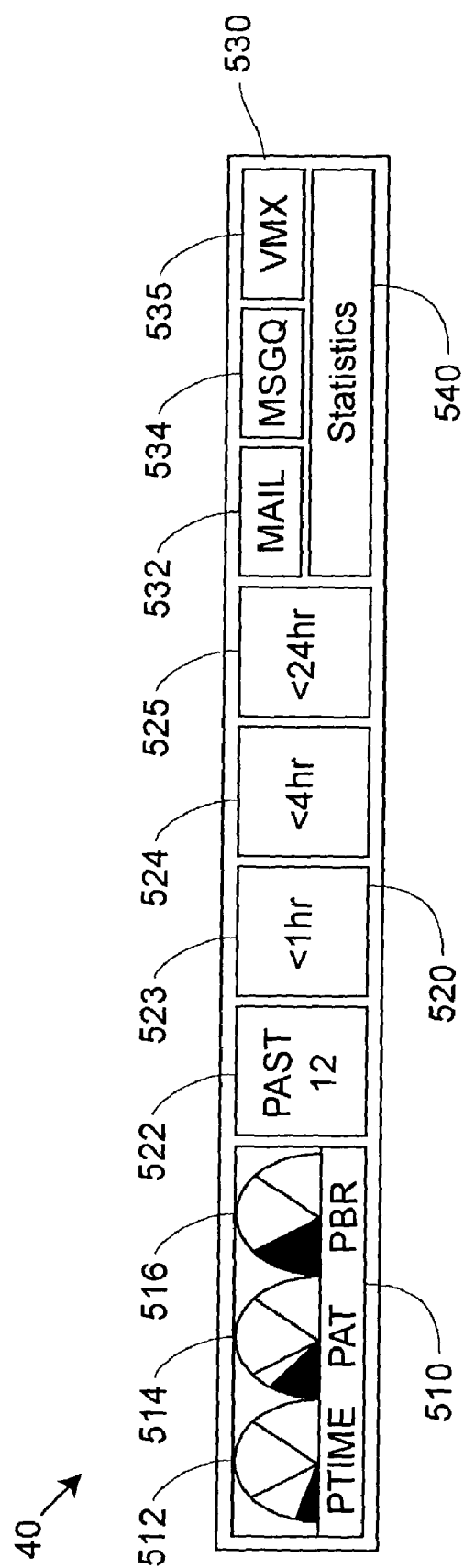
FIG. 14 is a graphic display of a dashboard.

Although only one dashboard configuration is described herein, the dashboard 40 may be configured in a number of ways and may display various combinations of data, depending on the needs of the pharmacy and the pharmacy staff. Referring to FIG. 14, the dashboard 40, 42 is divided into four areas: a gauge area 510, an exceptions area 520, an alerts area 530, and a statistics area 540. The gauge area 510 may represent time-sensitive data and may be further divided into three sections: a promised time (PTIME) 512 section, a patient hold time (PAT) 514 section, and a prescriber hold time (PBR) 516 section. Based on the promised times, the PTIME 512 may be an indicator of the wait time associated with prescriptions for patients currently waiting in the pharmacy. The PTIME 512 may also reflect those prescriptions printed and verified during the previous ninety-minute time span. Thus, the PTIME 512 is a partial summary of the promised times generated by the ALPS 26 as discussed above. The PTIME 512 may be further divided into three wedges: wedge #1, wedge #2, and wedge #3, with each wedge having a different color representing a different wait time range. For example, wedge #1 may be shown in green to represent a wait time of less than or equal to 15 minutes, wedge #2 may be shown in yellow to represent a wait time of between 15 minutes and less than or equal to 30 minutes, and wedge #3 may be shown in red to represent a wait time of greater than 30 minutes.

The PAT 514 may be configured to display current telephone hold times for patients requesting a prescription or for patients inquiring about a prescription. As with the PTIME 512, the PAT 514 may be divided into three wedges, wedge #1, wedge #2, and wedge #3, with each wedge having a different color representing a different wait time range. For example, wedge #1 may be shown in green to represent a wait time of less than 10 seconds, wedge #2 may be shown in yellow to represent a wait time of between 11 and 20 seconds, and wedge #3 may be shown in red to represent a wait time of greater than 20 seconds. Similarly, the PBR 516 may be divided into three wedges: wedge #1, wedge #2, and wedge #3, with each wedge having a different color representing a different wait-time range. For example, wedge #1 may be shown in green to represent a wait time of less than 10 seconds, wedge #2 may be shown in yellow to represent a wait time of between 11 and 20 seconds, and wedge #3 may be shown in red to represent a wait time of greater than 20 seconds.

The exceptions area 520 may display a number of pushbuttons: pushbutton 522, pushbutton 523, pushbutton 524, and pushbutton 525, with each push button representing a category of promised times for a number of prescription/exceptions having promised times falling within a specific time range. For example, pushbutton 522 may represent the prescriptions with exceptions having promised times past the current time. When the pushbutton 522 is selected, the graphic display shown in FIG. 7 may be displayed on the user interface 36. Similarly, pushbutton 523 may represent the prescriptions with exceptions having promised times less than an hour from the current time. Pushbutton 524 may represent the prescriptions with exceptions having promised times less than four hours from the current time. Pushbutton 525 may represent the prescriptions with exceptions having promised times less than four hours from the current time.

The alerts area 530 may display alerts associated with operation of the pharmacy 6. For example, the alerts area 530 may display an icon for e-mail (MAIL) 532, messages generated by touch-tone prescription phone orders (MSGQ) 534 that could not be filled automatically, or EDI prescriptions that could not be filled automatically because, for example, the drug is discontinued. The alerts area 530 may also display an icon for voice mail messages (VMX) 535. The MAIL 532 icon may alert the pharmacy staff that an e-mail has been received via an Internet prescription service. The MAIL 532 icon may disappear when a pharmacy staff member opens the e-mail via the user interface or the workstation. Similarly, the MSGQ 534 icon may alert the pharmacy staff that a new prescription has been received via a message queue. The MSGQ 534 icon may disappear when a pharmacy staff member opens the message queue via the user interface or the workstation. The VMX 535 icon may alert the pharmacy staff that a patient and/or prescriber voice mail message has been received: The VMX 535 icon may disappear when a pharmacy staff member listens to the voicemail via a telephone.

The statistics area 540 may also display a pushbutton. When selected, the pushbutton may cause data representing prescription statistics to be displayed on the user interface 36. The prescription statistics may include, but are not limited to, (1) the current time prescription statistics for entered, printed, ready, and sold prescriptions, (2) the prescriptions that were entered by not printed with promised times of less than an hour, less than four hours, and less than twenty-four hours, and (3) prescriptions printed and filled but not verified with promised times of less than an hour, less than four hours, and less than twenty-four hours.

Although the technique for automating the prescription workflow 52 from receipt of the prescription order to delivery of the prescription to the patient as described herein is particularly well suited to be implemented in software, it may be implemented in hardware, firmware, or by any other processor associated with the store. Thus, the routines described herein may be implemented in a standard multi-purpose CPU or on specifically designed hardware or firmware as desired. When implemented in software, the software routine may be stored in any computer readable memory such as, but not limited to, a magnetic disk, a laser disk, and a RAM or ROM of a computer or processor. Likewise, the software may be delivered to a user or process control system via any known or desired delivery method including, for example, on a computer readable disk or other transportable computer storage mechanism or over a communication channel such as, but not limited to, a telephone line, and the Internet (which are viewed as being the same as or interchangeable with providing such software via transportable storage medium).

Many changes and modifications to the embodiments described herein could be made. The scope of some changes is discussed above. The scope of others will become apparent from the appended claims.

What is claimed is:

1. A method for processing an order for a prescription, the method implemented by a computer apparatus programmed to perform the method, the method comprising:
    generating by the computer apparatus a scheduled delivery time for the prescription order, the scheduled delivery time being a time when the prescription associated with the prescription order is estimated to be ready for delivery to the patient and being based on information received from the patient;
    printing a prescription label for the prescription order, the prescription label being printed according to the prescription order's priority among one or more other prescription orders, the priority based on at least the scheduled delivery time such that a first prescription label having an earlier scheduled delivery time is printed before a second prescription label having a later scheduled delivery time;
    providing to pharmacy personnel an indication of each prescription order's priority among all of the prescription orders;
    generating by the computer apparatus, based on the prescription label, a plurality of graphical verification displays to facilitate verification of the prescription order by the pharmacy personnel;
    generating by the computer apparatus a plurality of statistics, the statistics displayed as one or more graphs and providing information related to a number of prescription orders entered into the system, a number of prescription labels printed, a number of prescriptions ready for delivery, a number of prescriptions sold, a number of prescription orders entered but for which labels have not been printed, or a number of prescription orders for which labels have been printed and orders filled but which have not been verified; and
    notifying the patient of the status of the prescription associated with the prescription order based on the displayed statistics.

2. The method of claim 1, wherein the priority is based on either (1) the scheduled delivery time associated with the prescription order and an identification parameter associated with the patient, or (2) the scheduled delivery time, a current volume of other prescription orders within a queue of a pharmacy, and an identification parameter associated with the patient.

3. The method of claim 1, wherein the step of printing a prescription label comprises printing a prescription label having a bar code configured to verify the prescription order.

4. The method of claim 1, wherein the step of printing a prescription label comprises:
    printing the prescription label for the prescription in response to the scheduled delivery time being within a first time period of the current time and being past the current time by less than a second time period.

5. The method of claim 4, wherein the step of generating a scheduled delivery time comprises:
    determining whether a wait period has elapsed since a prior scheduled delivery time was generated in response to one or more prior prescription labels being generated within a third time period, the prior scheduled delivery time being associated with a prior prescription order;
    determining a number of verified prescription labels from the one or more prior prescription labels generated during the third time period;
    determining an average generated-to-verified time from generating the one or more prior prescription labels to verifying the one or more prior prescription labels based on the number of verified prescription labels;
    determining a verification time based on the average generated-to-verified time and a buffer time; and
    determining the scheduled delivery time based on the verification time and the current time.

6. The method of claim 1, wherein the step of printing a prescription label comprises:
    printing a plurality of prescription labels in response to the scheduled delivery time being within a first time period of the current time and being past the current time by greater than a second time period based on one of the operation hours of the pharmacy, the number of prescription orders to be processed, and the number of times that a calculation of prescription labels to be printed is performed in a third time period.

7. The method of claim 1, wherein the step of generating a plurality of graphical verification displays comprises:
    scanning a bar code associated with the prescription label; and
    generating a plurality of graphical verification displays based on the bar code, the plurality of graphical verification displays having information associated with the prescription order.

8. The method of claim 1, wherein the step of generating a plurality of statistics comprises generating and displaying at least one graph configured to display a condition suggesting a potential for a delay of the delivery to the patient of a prescription, and wherein the condition suggesting a potential for a delay of the prescription is one of a condition associated with a prescriber of the prescription, a condition associated with allocation of drugs for the prescription, and a condition associated with insurance coverage of the patient.

9. The method of claim 1, wherein the step of notifying the patient comprises notifying the patient that the prescription will not be ready by the scheduled delivery time in response to the prescription order being unfilled, unverified, or having an unresolved condition suggesting a potential for a delay of the delivery of the prescription to the patient.

10. In a system having a computer operating in accordance with a computer program embodied on a computer-readable medium for processing a prescription order, wherein the computer includes a memory and a processor operatively coupled to the memory, the computer program comprising:
    a first routine that directs the processor to generate a scheduled delivery time for the prescription order, the scheduled delivery time being a time when the prescription associated with the prescription order is estimated to be ready for delivery to the patient and being based on information received from the patient;

a second routine that directs the processor to print a prescription label for the prescription order, the prescription label being printed according to the prescription order's priority among one or more other prescription orders, the priority based on at least the scheduled delivery time such that a first prescription label having an earlier scheduled delivery time is printed before a second prescription label having a later scheduled delivery time;

a third routine that directs the processor to generate a plurality of graphical verification displays to facilitate verification of the prescription order by pharmacy personnel after the prescription order is filled;

a fourth routine that directs the processor to generate a plurality of statistics, the statistics displayed as one or more graphs and providing information related to a number of prescription orders entered into the system, a number of prescription labels printed, a number of prescriptions ready for delivery to the patient, a number of prescriptions sold, a number of prescription orders entered but for which labels have not been printed, or a number of prescription orders for which labels have been printed and orders filled but which have not been verified; and a fifth routine that directs the processor to notify the patient of the status of the prescription associated with the prescription order based on the displayed statistics.

11. The computer program of claim 10, wherein the priority is based on either (1) the scheduled delivery time associated with the prescription order and an identification parameter associated with the patient, or (2) the scheduled delivery time, a current volume of other prescription orders within a queue of a pharmacy, and an identification parameter associated with the patient.

12. The computer program of claim 10, wherein the second routine directs the processor to print a prescription label having a bar code configured to verify the prescription order.

13. The computer program of claim 10, wherein the second routine directs the processor to print the prescription label for the prescription in response to the scheduled delivery time being within a first time period of the current time and being past the current time by less than a second time period.

14. The computer program of claim 13, wherein the first routine:
   directs the processor to determine whether a wait period has elapsed since a prior scheduled delivery time was generated in response to one or more prior prescription labels being printed within a third time period, the prior scheduled delivery time being associated with a prior prescription order;
   directs the processor to determine a number of verified prescription labels from the one or more prior prescription labels printed during the third time period;
   directs the processor to determine an average generated-to-verified time from printing the one or more prior prescription labels to verifying the one or more prior prescription labels based on the number of verified prescription labels;
   directs the processor to determine a verification time based on the average generated-to-verified time and a buffer time; and
   directs the processor to determine the scheduled delivery time based on the verification time and the current time.

15. The computer program of claim 10, wherein the second routine:
   directs the processor to print a plurality of prescription labels in response to the scheduled delivery time being within a first time period of the current time and being past the current time by greater than a second time period based on one of the operation hours of the pharmacy, the number of prescription orders to be processed, and the number of times that a calculation of prescription labels to be printed is performed in a third time period.

16. The computer program of claim 10, wherein the third routine:
   directs the processor to scan a bar code associated with the prescription label; and
   directs the processor to generate a plurality of graphical verification displays based on the bar code, the plurality of graphical verification displays having information associated with the prescription order.

17. The computer program of claim 10, wherein the third routine directs the processor to generate and display at least one graph configured to display a condition suggesting a potential for a delay of the delivery to the patient of a prescription, and wherein the condition suggesting a potential for a delay of the prescription is one of a condition associated with a prescriber of the prescription, a condition associated with allocation of drugs for the prescription, and a condition associated with insurance coverage of the patient.

18. The computer program of claim 10, wherein the fifth routine directs the processor to notify the patient that the prescription will not be ready by the scheduled delivery time in response to the prescription order being unfilled, unverified, or having an unresolved condition suggesting a potential for a delay of the delivery of the prescription to the patient.

19. A system for processing a prescription order, the system comprising:
   a workstation having a user interface, the user interface configured to generate a graphical display;
   a printing device configured to generate a prescription label; and
   a controller operatively coupled to the workstation and the printing device, the controller having a memory and a processor, the processor operatively coupled to the memory,
   the controller being programmed to:
   generate a scheduled delivery time for the prescription order, the scheduled delivery time being a time when the prescription associated with the prescription order is estimated to be ready for delivery to the patient and being based on information received from the patient;
   print a prescription label for a prescription order, according to the prescription order's priority among one or more other prescription orders, the priority based on at least the scheduled delivery time such that a first prescription label having an earlier scheduled delivery time is printed before a second prescription label having a later scheduled delivery time;
   generate, via the user interface, a plurality of graphical verification displays to facilitate verification of the prescription order by pharmacy personnel after the prescription order is filled;
   generate a plurality of statistics, the statistics displayed as one or more graphs and providing information related to a number of prescription orders entered into the system, a number of prescription labels printed, a number of prescriptions ready for delivery to the patient, a number of prescriptions sold, a number of prescription orders entered but for which labels have not been printed, or a number of prescription orders for which labels have been printed and orders filled but which have not been verified; and notify the patient of the status of the prescription associated with the prescription order based on the displayed statistics.

20. The system of claim 19, wherein the controller is programmed to the priority based on either (1) the scheduled delivery time associated with the prescription order and an identification parameter associated with the patient, or (2) the scheduled delivery time, a current volume of other prescription orders within a queue of a pharmacy, and an identification parameter associated with the patient.

21. The system of claim 19, wherein the controller is programmed to print a prescription label having a bar code configured to verify the prescription order.

22. The system of claim 19, wherein the controller is programmed to print the prescription label for the prescription in response to the scheduled delivery time being within a first time period of the current time and being past the current time by less than a second time period.

23. The system of claim 22, wherein the controller is programmed to determine whether a wait period has elapsed since a prior scheduled delivery time was generated in response to one or more prior prescription labels being generating within a third time period, to determine a number of verified prescription labels from the one or more prior prescription labels generated during the third time period, to determine an average generated-to-verified time from generating the one or more prior prescription labels to verifying the one or more prior prescription labels based on the number of verified prescription labels, to determine a verification time based on the average generated-to-verified time and a buffer time, and to determine the scheduled delivery time based on the verification time and the current time, and wherein the prior scheduled delivery time is associated with a prior prescription order.

24. The system of claim 19, wherein the controller is programmed to print a plurality of prescription labels in response to the scheduled delivery time being within a first time period of the current time and being past the current time by greater than a second time period based on one of the operation hours of the pharmacy, the number of prescription orders to be processed, and the number of times that a calculation of prescription labels to be printed is performed in a third time period.

25. The system of claim 19, wherein the controller is programmed to scan a bar code associated with the prescription label and to generate a plurality of graphical verification displays based on the bar code, the plurality of graphical verification displays having information associated with the prescription order.

26. The system of claim 19, wherein the controller is programmed to generate and display at least one graph configured to display a condition suggesting a potential for a delay of the delivery to the patient of a prescription, and wherein the condition suggesting a potential for a delay of the prescription is one of a condition associated with a prescriber of the prescription, a condition associated with allocation of drugs for the prescription, and a condition associated with insurance coverage of the patient.

27. The system of claim 19, wherein the controller is programmed to notify the patient that the prescription will not be ready by the scheduled delivery time in response to the prescription order being unfilled, unverified, or having an unresolved condition suggesting a potential for a delay of the delivery of the prescription to the patient.

28. The system of claim 19, wherein the memory comprises one of a hard disk, a floppy disk, a memory card, a memory stick, a compact disc, a digital versatile disc, a magnetic memory, a read-only memory, an erasable programmable read-only memory, a random-access memory, and an optical memory.

* * * * *